(12) United States Patent
Fuchiwaki

(10) Patent No.: US 10,522,760 B2
(45) Date of Patent: Dec. 31, 2019

(54) POLYCYCLIC COMPOUND AND ORGANIC ELECTROLUMINESCENCE DEVICE INCLUDING THE SAME

(71) Applicant: SAMSUNG DISPLAY CO., LTD., Yongin-si, Gyeonggi-do (KR)

(72) Inventor: Junta Fuchiwaki, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 192 days.

(21) Appl. No.: 15/684,112

(22) Filed: Aug. 23, 2017

(65) Prior Publication Data
US 2018/0097181 A1 Apr. 5, 2018

(30) Foreign Application Priority Data

Oct. 4, 2016 (KR) ........................ 10-2016-0127782

(51) Int. Cl.
*H01L 51/00* (2006.01)
*C07F 7/08* (2006.01)
*H01L 51/50* (2006.01)

(52) U.S. Cl.
CPC ........ *H01L 51/0035* (2013.01); *C07F 7/0816* (2013.01); *H01L 51/0071* (2013.01);
(Continued)

(58) Field of Classification Search
None
See application file for complete search history.

(56) References Cited

U.S. PATENT DOCUMENTS 8,927,749 B2 1/2015 Boudreault et al.
2010/0171417 A1 7/2010 Kitamura et al.
(Continued)

FOREIGN PATENT DOCUMENTS

CN 105859714 A * 8/2016 ........... C07D 471/04
KR 10-2006-0032930 A 4/2006
(Continued)

OTHER PUBLICATIONS

Ito et al. "para-Phenylene-Bridged Spirobi(triarylamine) Dimer with Four Perpendicularly Linked Redox-Active Pi Systems" Chem. Eur. J. 2010, 16, 10866-10878. (Year: 2010).*
(Continued)

*Primary Examiner* — Robert S Loewe
(74) *Attorney, Agent, or Firm* — Lewis Roca Rothgerber Christie LLP

(57) ABSTRACT

A polycyclic compound and an organic electroluminescence device, the polycyclic compound being represented by the following Formula 1:

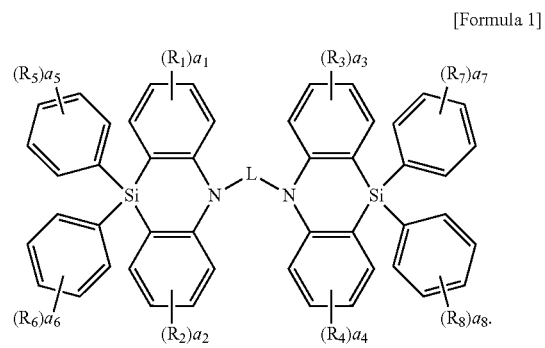

14 Claims, 2 Drawing Sheets

(52) U.S. Cl.
CPC ...... *H01L 51/0094* (2013.01); *H01L 51/5012* (2013.01); *H01L 51/5096* (2013.01)

(56) References Cited

U.S. PATENT DOCUMENTS

| | | |
|---|---|---|
| 2015/0188056 A1 | 7/2015 | Suda |
| 2017/0263871 A1* | 9/2017 | Wang ..................... H05B 33/14 |
| 2018/0205019 A1* | 7/2018 | Fuchiwaki .......... H01L 51/0059 |

FOREIGN PATENT DOCUMENTS

| | | | | |
|---|---|---|---|---|
| KR | 10-2015-0033700 A | | 4/2015 | |
| KR | 20160073914 A | * | 6/2016 | ................ C07F 7/08 |
| WO | WO 2007/110228 A1 | | 10/2007 | |
| WO | WO-2011136484 A1 | * | 11/2011 | .......... C07C 211/61 |
| WO | WO 2014/002629 A1 | | 5/2016 | |

OTHER PUBLICATIONS

Machine translation of KR-20160073914, translation generated Apr. 2019, 35 pages. (Year: 2019).*

* cited by examiner

POLYCYCLIC COMPOUND AND ORGANIC ELECTROLUMINESCENCE DEVICE INCLUDING THE SAME

CROSS-REFERENCE TO RELATED APPLICATIONS

Korean Patent Application No. 10-2016-0127782, filed on Oct. 4, 2016, in the Korean Intellectual Property Office, and entitled: "Polycyclic Compound and Organic Electroluminescence Device Including the Same," is incorporated by reference herein in its entirety.

BACKGROUND

1. Field

Embodiments relate to a polycyclic compound and an organic electroluminescence device including the same.

2. Description of the Related Art

The development of an organic electroluminescence display as an image display is being actively conducted. An organic electroluminescence display is different from a liquid crystal display and is a self-luminescent display accomplishing displays via the recombination of holes and electrons injected from a first electrode and a second electrode in an emission layer and the light emission from a luminescent material which is an organic compound included in the emission layer.

The organic electroluminescence device may include, e.g., a first electrode, a hole transport layer disposed on the first electrode, an emission layer disposed on the hole transport layer, an electron transport layer disposed on the emission layer, and a second electrode disposed on the electron transport layer. Holes are injected from the first electrode, and the injected holes move via the hole transport layer and are injected into the emission layer. Meanwhile, electrons are injected from the second electrode, and the injected electrons move via the electron transport layer and are injected into the emission layer. The holes and the electrons, which are injected into the emission layer, recombine to produce excitons in the emission layer. The organic electroluminescence device may emit light using light generated by the transition of the excitons to a ground state.

SUMMARY

Embodiments are directed to a polycyclic compound and an organic electroluminescence device including the same.

The embodiments may be realized by providing a polycyclic compound represented by the following Formula 1:

[Formula 1]

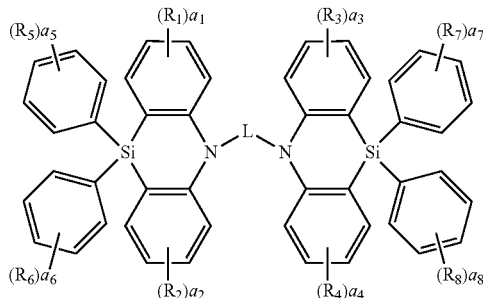

wherein, in Formula 1, L is a substituted or unsubstituted arylene group having 6 to 30 ring carbon atoms, $R_1$ to $R_8$ are each independently a hydrogen atom, a deuterium atom, a halogen atom, a cyano group, a substituted or unsubstituted silyl group, an alkyl group having 1 to 20 carbon atoms, a substituted or unsubstituted aryl group having 6 to 30 ring carbon atoms, or a substituted or unsubstituted heteroaryl group having 2 to 30 ring carbon atoms, $a_1$ to $a_4$ are each independently an integer of 0 to 4, and $a_5$ to $a_8$ are each independently an integer of 0 to 5.

L may be a substituted or unsubstituted phenylene group.

L may be a substituted or unsubstituted divalent biphenyl group.

L may be a substituted or unsubstituted divalent terphenyl group.

L may be a substituted or unsubstituted fluorenylene group.

L may be a group represented by one of the following Formulae 2-1 to 2-8:

[Formula 2-1]

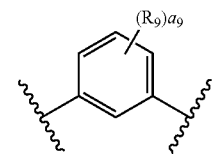

[Formula 2-2]

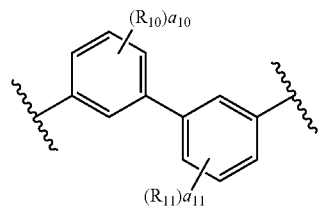

[Formula 2-3]

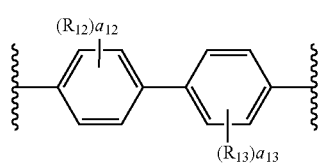

[Formula 2-4]

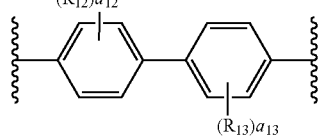

[Formula 2-5]

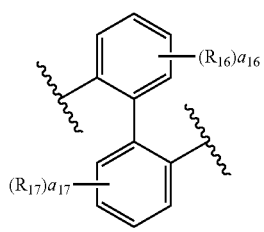

-continued

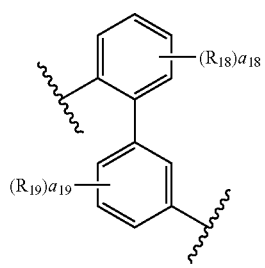
[Formula 2-6]

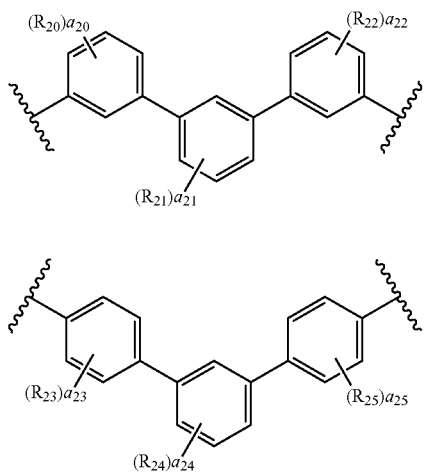
[Formula 2-7]

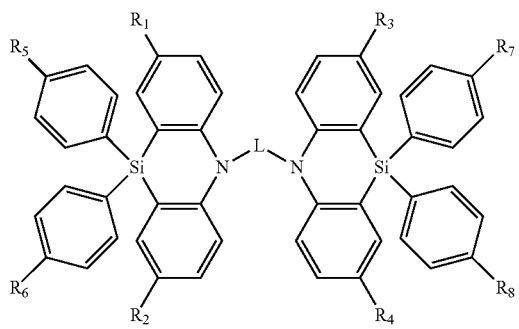
[Formula 2-8]

wherein, in Formulae 2-1 to 2-8, $R_9$ to $R_{25}$ may each independently be a hydrogen atom, a deuterium atom, a halogen atom, a cyano group, a substituted or unsubstituted silyl group, an alkyl group having 1 to 20 carbon atoms, a substituted or unsubstituted aryl group having 6 to 30 ring carbon atoms, or a substituted or unsubstituted heteroaryl group having 2 to 30 ring carbon atoms, $R_9$ to $R_{25}$ may be separate or combine with an adjacent group to form a ring, and $a_9$ to $a_{25}$ may each independently be an integer of 0 to 4.

The polycyclic compound represented by Formula 1 may be represented by the following Formula 3:

[Formula 3]

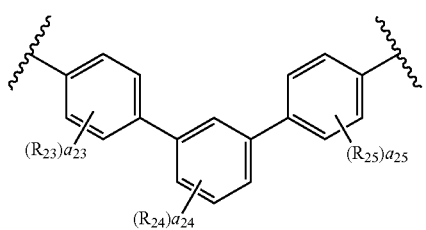

wherein, in Formula 3, L may be a substituted or unsubstituted arylene group having 6 to 30 ring carbon atoms, $R_1$ to $R_8$ may each independently be a hydrogen atom, a deuterium atom, a halogen atom, a cyano group, a substituted or unsubstituted silyl group, an alkyl group having 1 to 20 carbon atoms, a substituted or unsubstituted aryl group having 6 to 30 ring carbon atoms, or a substituted or unsubstituted heteroaryl group having 2 to 30 ring carbon atoms, and at least one of $R_1$ to $R_8$ may be a deuterium atom, a halogen atom, a cyano group, a substituted or unsubstituted silyl group, an alkyl group having 1 to 20 carbon atoms, a substituted or unsubstituted aryl group having 6 to 30 ring carbon atoms, or a substituted or unsubstituted heteroaryl group having 2 to 30 ring carbon atoms.

$R_1$ to $R_8$ may each independently be a hydrogen atom, a methyl group, a phenyl group, a fluorine atom, or a cyano group, and at least one of $R_1$ to $R_8$ may be a methyl group, a phenyl group, a fluorine atom, or a cyano group.

The polycyclic compound represented by Formula 1 may be one the following Compounds 1 to 27:

1

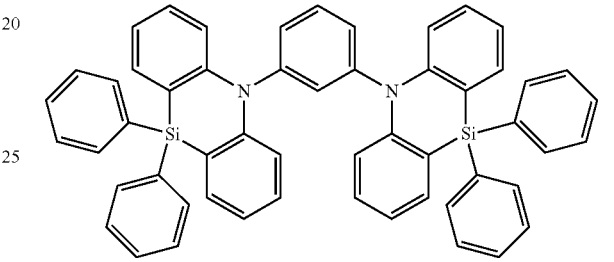

2

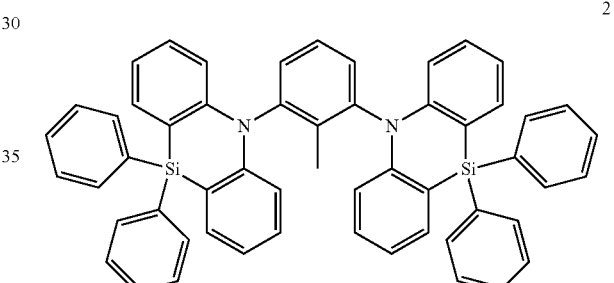

3

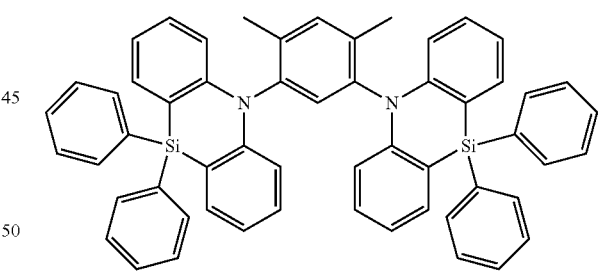

4

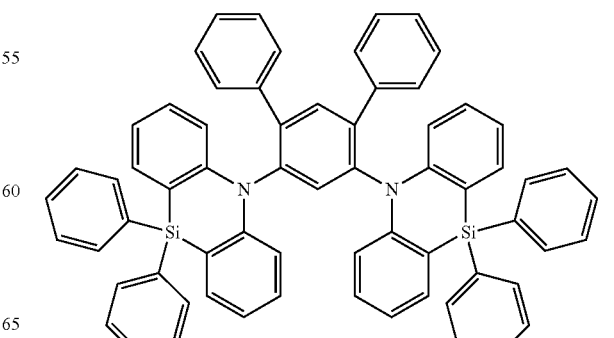

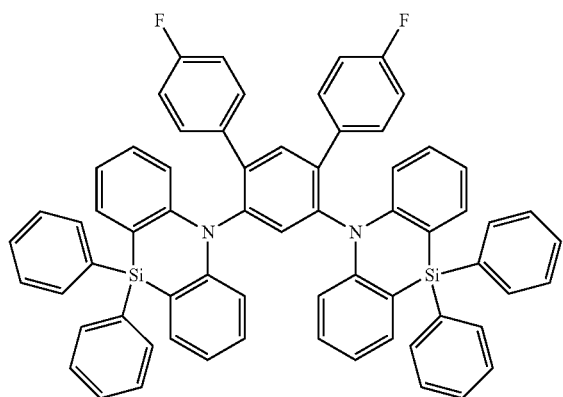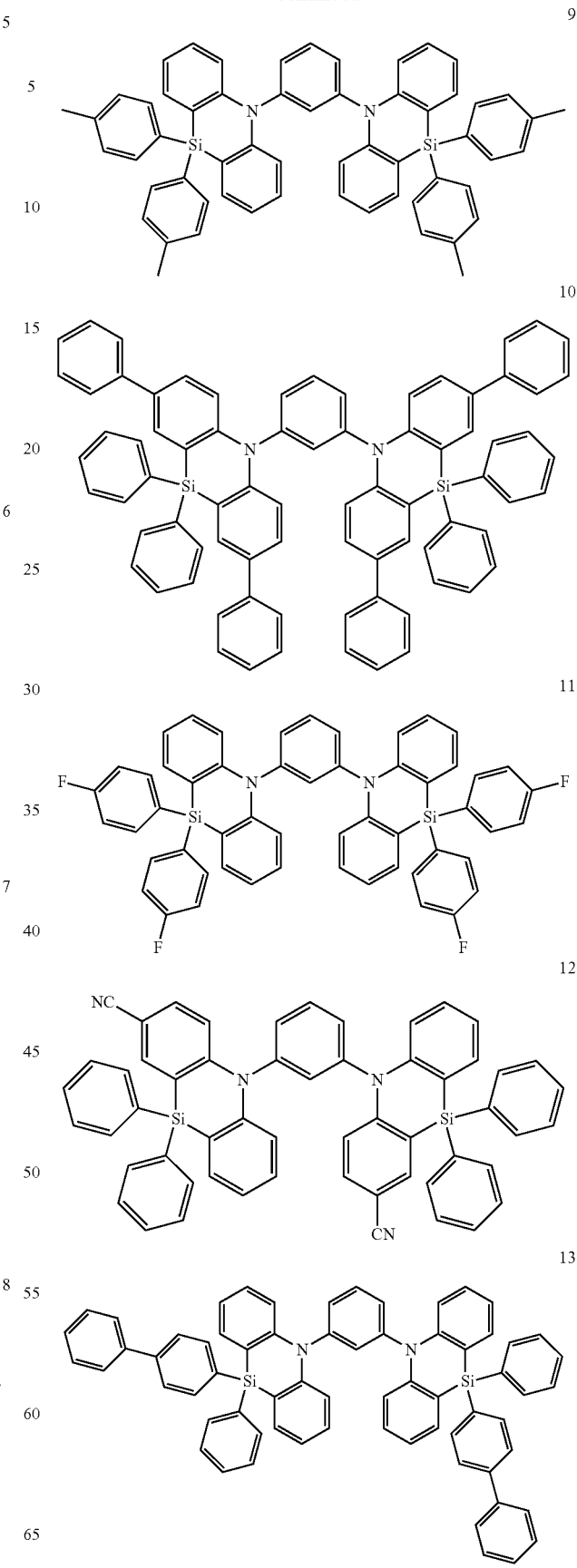

14
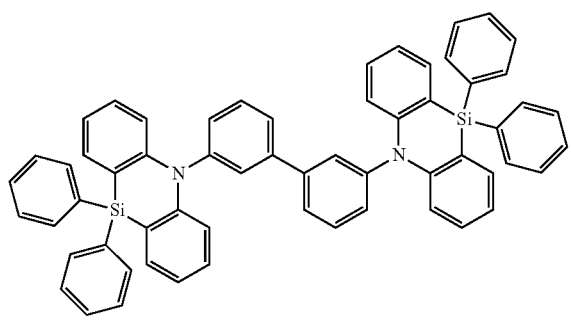
15
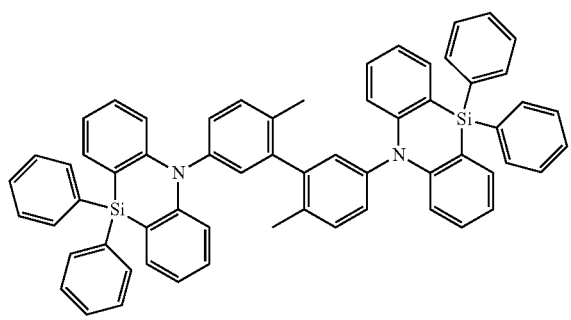
16
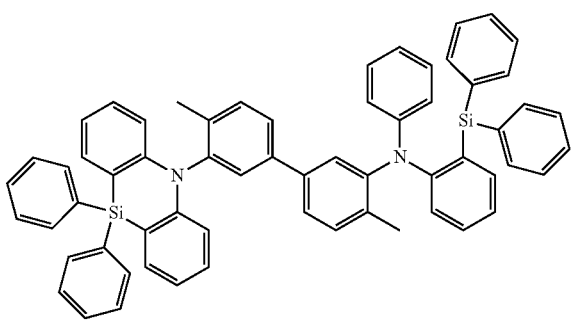
17
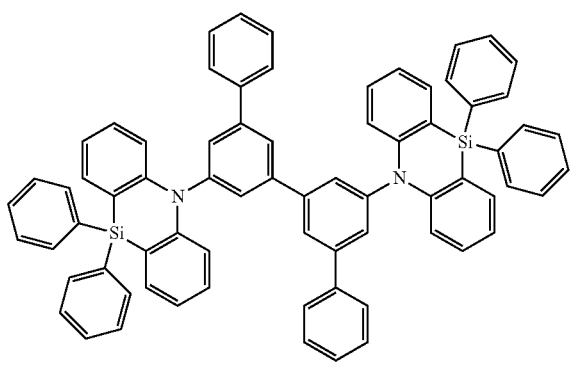
18
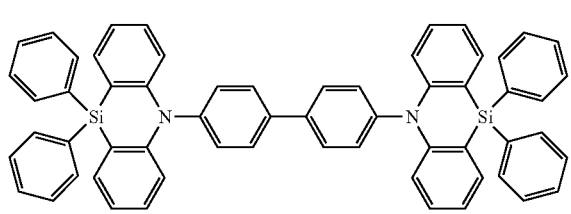
19
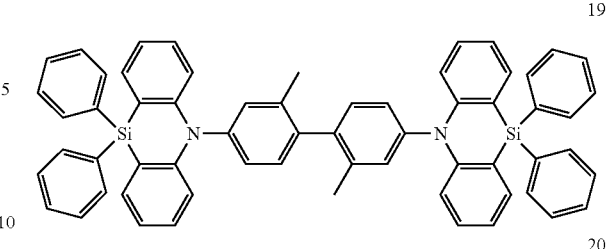
20
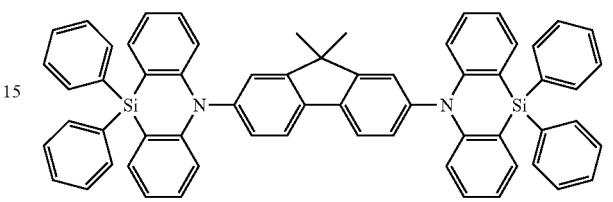
21
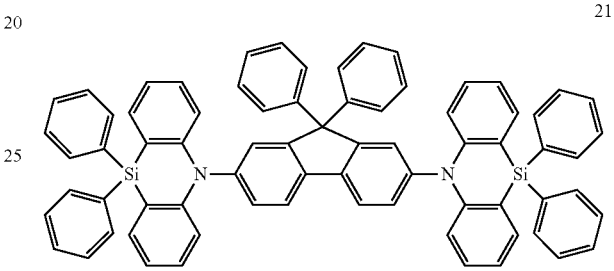
22
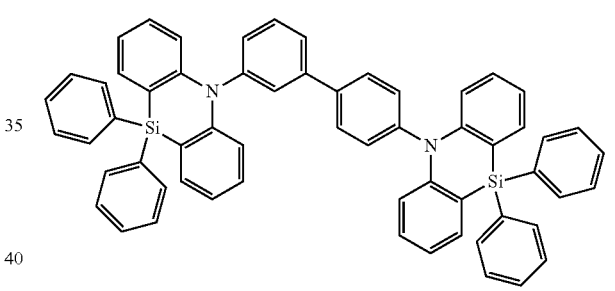
23
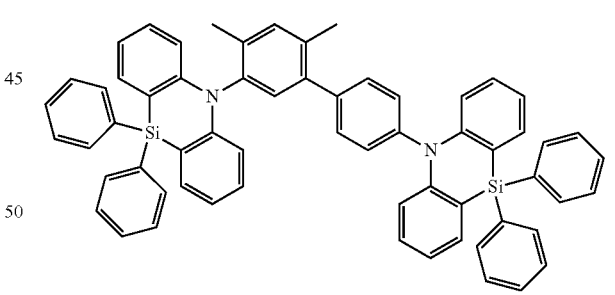
24
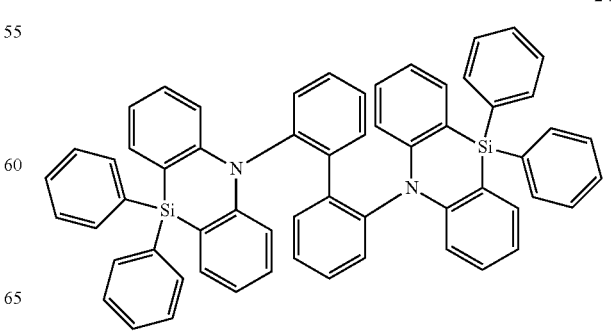

-continued

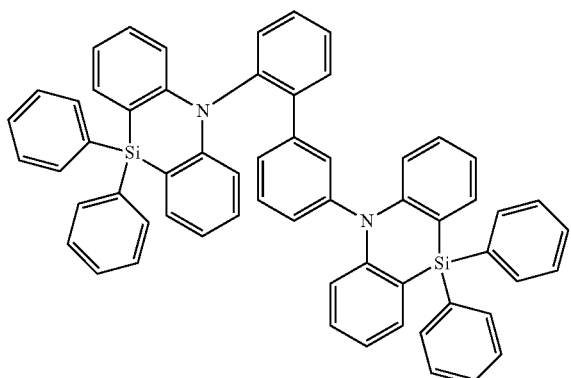

25

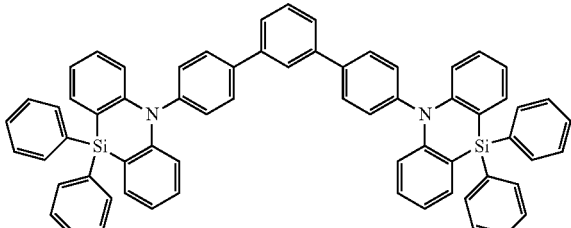

26

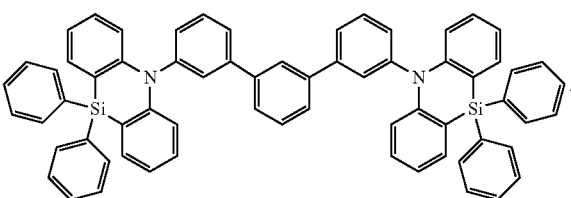

27

The embodiments may be realized by providing an organic electroluminescence device including a first electrode; a hole transport region disposed on the first electrode; an emission layer disposed on the hole transport region; an electron transport region disposed on the emission layer; and a second electrode disposed on the electron transport region, wherein the hole transport region includes a polycyclic compound represented by the following Formula 1:

[Formula 1]

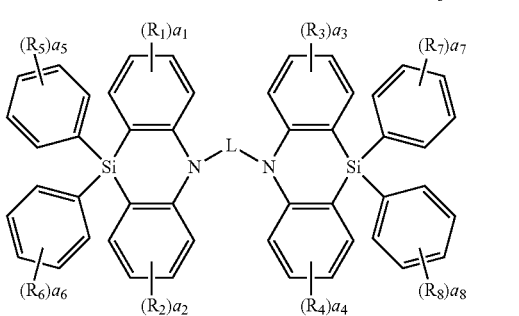

wherein, in Formula 1, L is a substituted or unsubstituted arylene group having 6 to 30 ring carbon atoms, $R_1$ to $R_8$ are each independently a hydrogen atom, a deuterium atom, a halogen atom, a cyano group, a substituted or unsubstituted silyl group, an alkyl group having 1 to 20 carbon atoms, a substituted or unsubstituted aryl group having 6 to 30 ring carbon atoms, or a substituted or unsubstituted heteroaryl group having 2 to 30 ring carbon atoms, $a_1$ to $a_4$ are each independently an integer of 0 to 4, and $a_5$ to $a_8$ are each independently an integer of 0 to 5.

The polycyclic compound represented by Formula 1 may have a lowest triplet energy level value of 3.2 eV or more.

L may be a substituted or unsubstituted phenylene group, a substituted or unsubstituted divalent biphenyl group, or a substituted or unsubstituted divalent terphenyl group.

L may be a substituted or unsubstituted fluorenylene group.

L may be a group represented by one of the following Formulae 2-1 to 2-8:

[Formula 2-1]

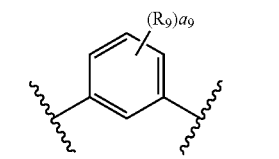

[Formula 2-2]

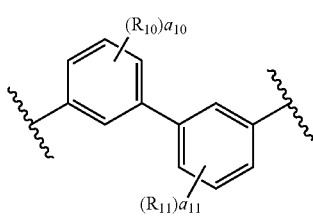

[Formula 2-3]

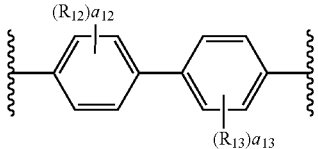

[Formula 2-4]

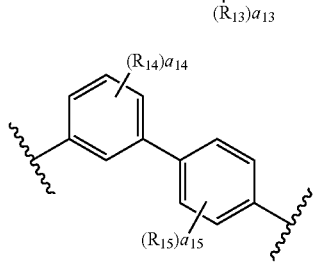

[Formula 2-5]

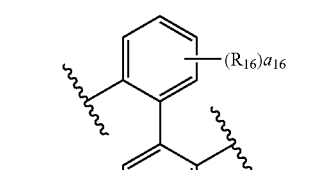

[Formula 2-6]

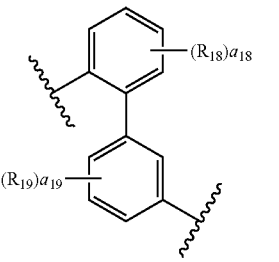

[Formula 2-7]

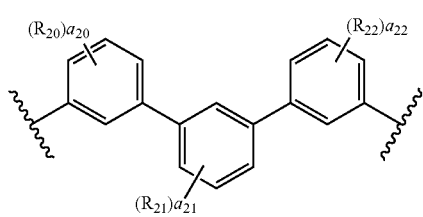

[Formula 2-8]

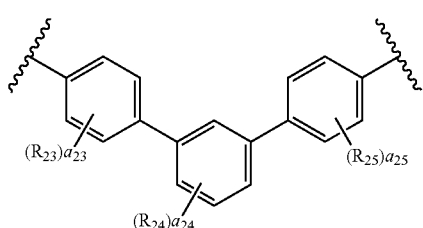

wherein, in Formulae 2-1 to 2-8, $R_9$ to $R_{25}$ may each independently be a hydrogen atom, a deuterium atom, a halogen atom, a cyano group, a substituted or unsubstituted silyl group, an alkyl group having 1 to 20 carbon atoms, a substituted or unsubstituted aryl group having 6 to 30 ring carbon atoms, or a substituted or unsubstituted heteroaryl group having 2 to 30 ring carbon atoms, $R_9$ to $R_{25}$ may be separate or combine with an adjacent group to form a ring, and $a_9$ to $a_{25}$ may each independently be an integer of 0 to 4.

The polycyclic compound represented by Formula 1 may be represented by the following Formula 3:

[Formula 3]

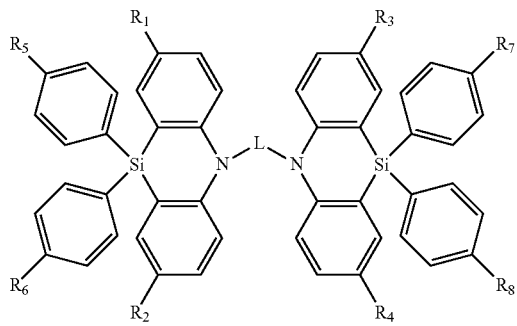

wherein, in Formula 3, L may be a substituted or unsubstituted arylene group having 6 to 30 ring carbon atoms, $R_1$ to $R_8$ may each independently be a hydrogen atom, a deuterium atom, a halogen atom, a cyano group, a substituted or unsubstituted silyl group, an alkyl group having 1 to 20 carbon atoms, a substituted or unsubstituted aryl group having 6 to 30 ring carbon atoms, or a substituted or unsubstituted heteroaryl group having 2 to 30 ring carbon atoms, and at least one of $R_1$ to $R_8$ may be a deuterium atom, a halogen atom, a cyano group, a substituted or unsubstituted silyl group, an alkyl group having 1 to 20 carbon atoms, a substituted or unsubstituted aryl group having 6 to 30 ring carbon atoms, or a substituted or unsubstituted heteroaryl group having 2 to 30 ring carbon atoms.

$R_1$ to $R_8$ may each independently be a hydrogen atom, a methyl group, a phenyl group, a fluorine atom, or a cyano group, and at least one of $R_1$ to $R_8$ may be a methyl group, a phenyl group, a fluorine atom, or a cyano group.

The polycyclic compound represented by Formula 1 may be one the following Compounds 1 to 27:

1

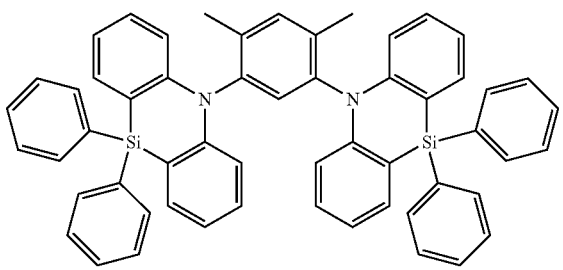

2

3

4

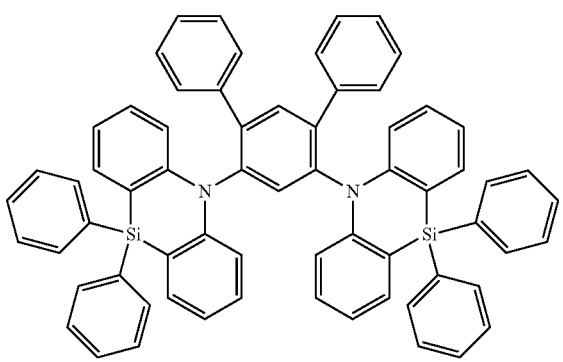

5
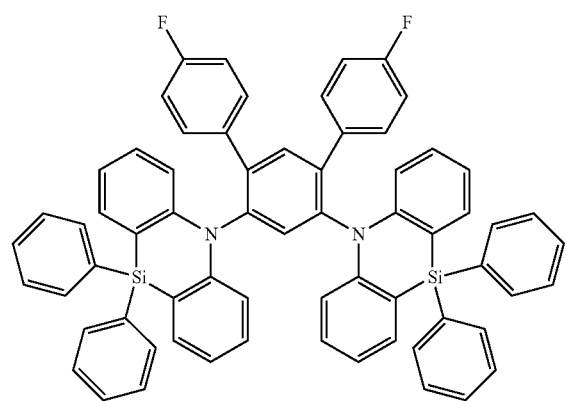
6
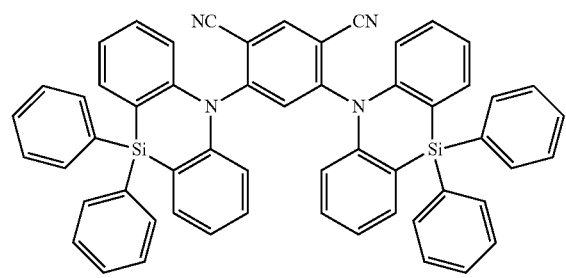
7
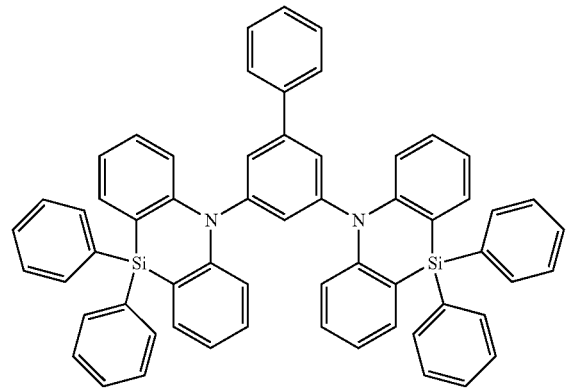
8
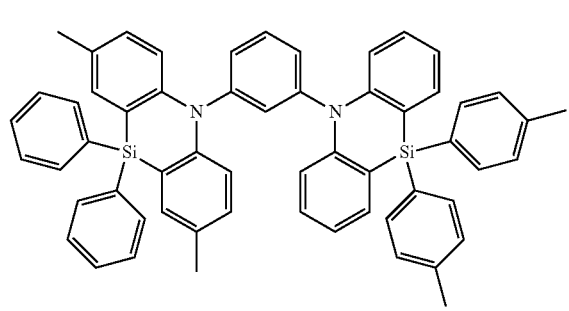
9
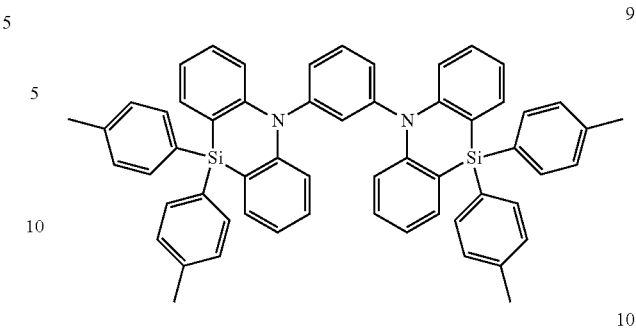
10
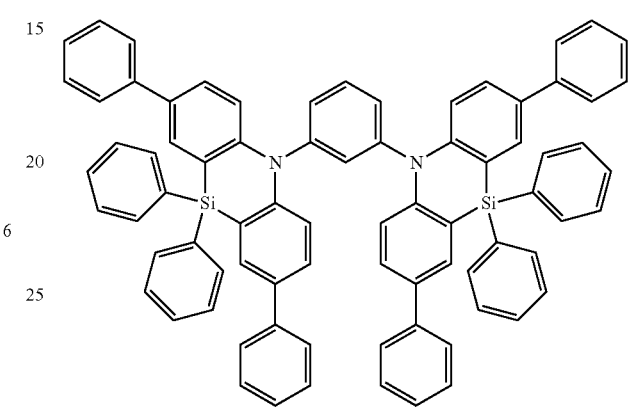
11
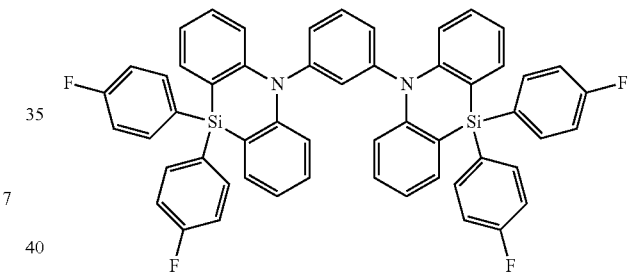
12
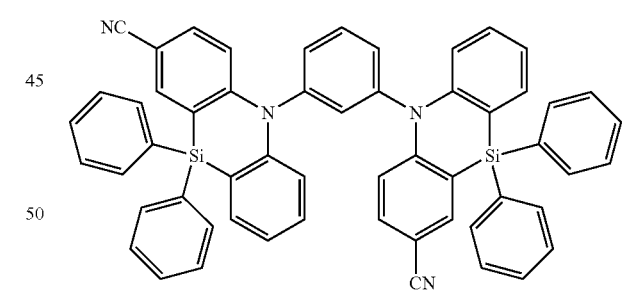
13
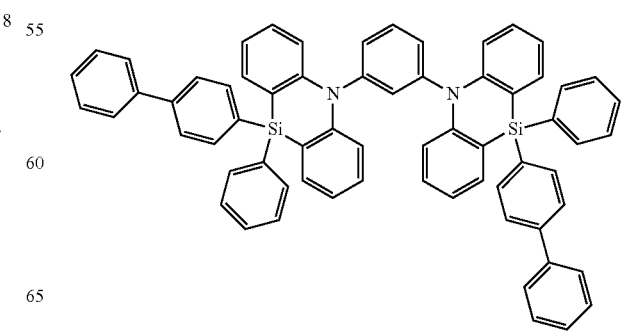

14
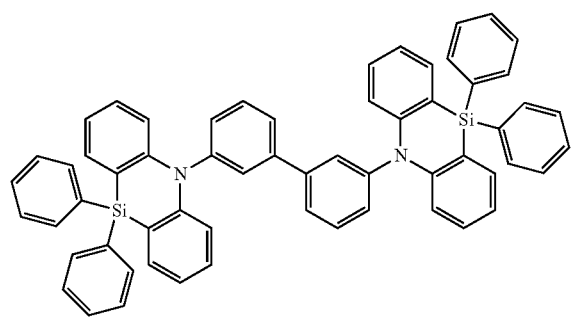
15
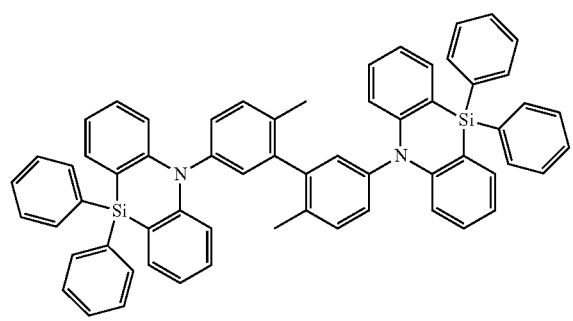
16
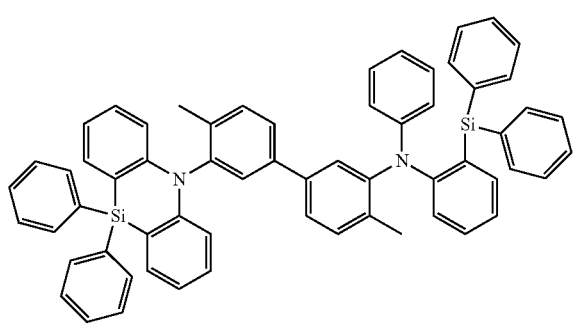
17
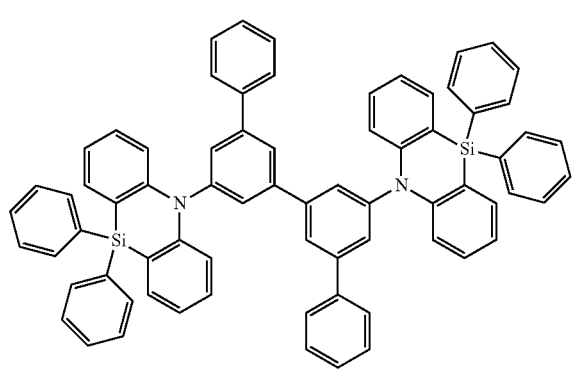
18
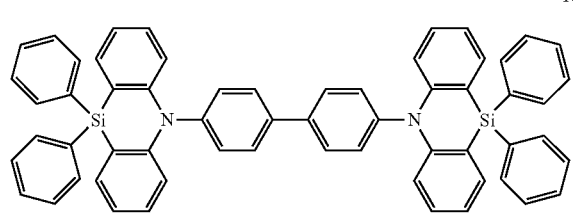
19
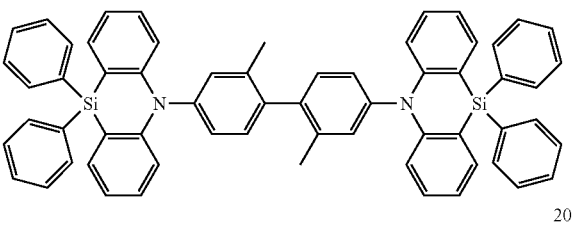
20
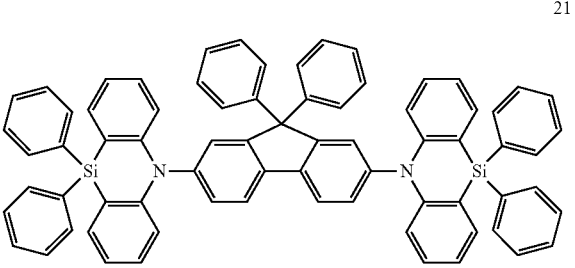
21
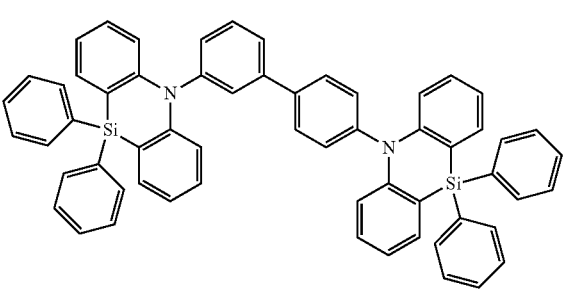
22
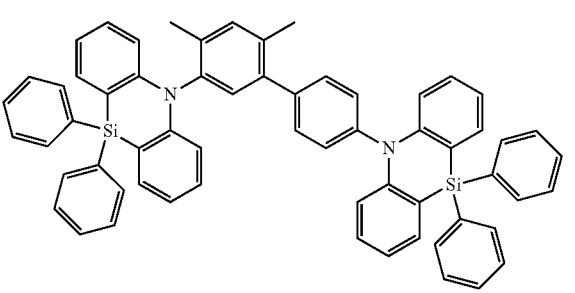
23
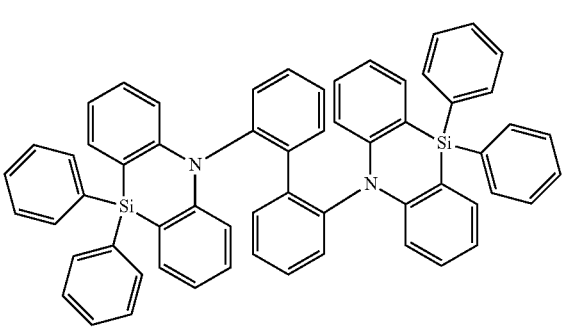
24

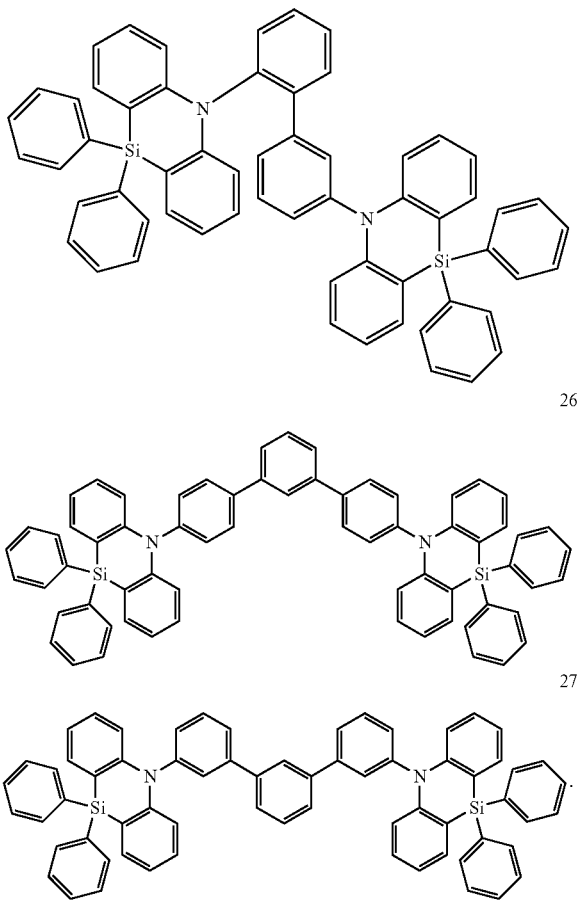

The hole transport region may include a hole injection layer; and a hole transport layer between the hole injection layer and the emission layer, the hole transport layer may include the polycyclic compound represented by Formula 1.

The hole transport region may include a hole injection layer; a hole transport layer on the hole injection layer; and an electron blocking layer between the hole transport layer and the emission layer, the electron blocking layer may include the polycyclic compound represented by Formula 1.

The polycyclic compound represented by Formula 1 may be a material emitting thermally activated delayed fluorescence (TADF) or a material emitting phosphorescence.

BRIEF DESCRIPTION OF THE FIGURES

Features will be apparent to those of skill in the art by describing in detail exemplary embodiments with reference to the attached drawings in which.

DETAILED DESCRIPTION

Figure 1:
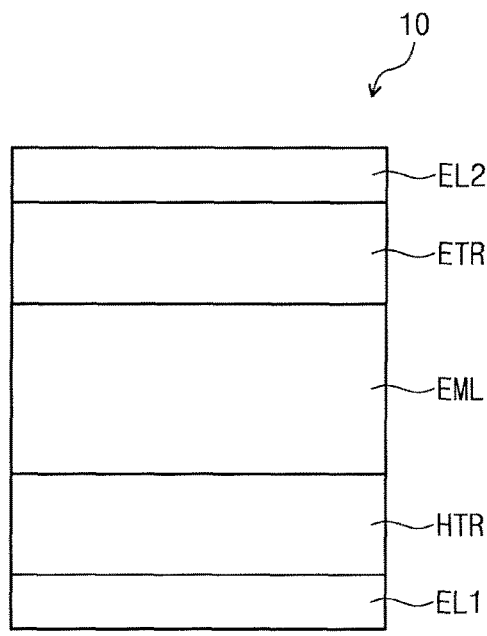
FIG. 1 illustrates a cross-sectional view schematically showing an organic electroluminescence device according to an embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

Like reference numerals refer to like elements for explaining each drawing. In the drawings, the sizes of elements may be enlarged for clarity. It will be understood that, although the terms first, second, etc. may be used herein to describe various elements, these elements should not be limited by these terms. These terms are only used to distinguish one element from another element. For example, a first element discussed below could be termed a second element, and similarly, a second element could be termed a first element. As used herein, the singular forms are intended to include the plural forms as well, unless the context clearly indicates otherwise.

It will be further understood that the terms "includes," "including," "comprises" or "comprising," when used in this specification, specify the presence of stated features, numerals, steps, operations, elements, parts, or a combination thereof, but do not preclude the presence or addition of one or more other features, numerals, steps, operations, elements, parts, or a combination thereof. It will also be understood that when a layer, a film, a region, a plate, etc. is referred to as being 'on' another part, it can be directly on the other part, or intervening layers may also be present. When a layer, a film, a region, a plate, etc. is referred to as being 'under' another part, it can be directly under the other part, or intervening layers may also be present.

In the present disclosure, means a part to be connected, e.g., a binding site.

In the present disclosure, "substituted or unsubstituted" may mean substituted with or including at least one substituent selected from the group of deuterium, halogen, cyano, nitro, amino, silyl, boron, arylamine, phosphine oxide, phosphine sulfide, alkyl, alkenyl, aryl, and heteroaryl or unsubstituted. In addition, each of the substituents may be substituted or unsubstituted. For example, biphenyl may be interpreted as aryl, or phenyl substituted with phenyl.

In the present disclosure, the descriptions relating to forming a ring by combining with an adjacent group may mean forming a substituted or unsubstituted hydrocarbon ring, or substituted or unsubstituted heterocycle by combining with an adjacent group each other. The hydrocarbon ring may include an aliphatic hydrocarbon ring and an aromatic hydrocarbon ring. The heterocycle may include an aliphatic heterocycle and aromatic heterocycle. The hydrocarbon ring and heterocycle may be a monocycle or polycycle. In addition, the ring formed by combining with an adjacent group may be connected with another ring to form a spiro structure.

In the present disclosure, the term "adjacent group" may mean a substituent substituted with an atom directly connected with another atom substituted with a corresponding substituent, a different substituent substituted with an atom substituted with a corresponding substituent, or a substituent disposed stereoscopically at the nearest position to a corresponding substituent. For example, two methyl groups in 1,2-dimethylbenzene may be interpreted as "adjacent groups" to each other, and two ethyl groups in 1,1-diethylcyclopentene may be interpreted as "adjacent groups" to each other.

In the present disclosure, halogen may include a fluorine atom, a chlorine atom, a bromine atom, or an iodine atom.

In the present disclosure, alkyl may have a linear or branched chain or a cycle type. The carbon number of the alkyl may be 1 to 30, 1 to 20, 1 to 15, 1 to 10, or 1 to 6. Examples of the alkyl may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldodecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyl eicosyl, 2-butyl eicosyl, 2-hexyl eicosyl, 2-octyl eicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the present disclosure, the aryl means a functional group or substituent derived from an aromatic hydrocarbon ring. The aryl may be monocyclic aryl or polycyclic aryl. The carbon number of the aryl for forming a ring may be 6 to 30, 6 to 20, or 6 to 15. Examples of the aryl may include phenyl, naphthyl, fluorenyl, anthracenyl, phenanthryl, biphenyl, terphenyl, quaterphenyl, quinqphenyl, sexiphenyl, triphenylene, pyrenyl, benzofluoranthenyl, chrysenyl, etc., without limitation.

In an implementation, in the present disclosure, the fluorenyl may be substituted, or two substituents may be combined with each other to form a spiro structure.

In the present disclosure, the heteroaryl may be heteroaryl including at least one of O, N, or S as a heteroatom. The carbon number of the heteroaryl for forming a ring may be 2 to 30, or 2 to 20. Examples of the heteroaryl may include thiophenyl, furanyl, pyrrolyl, imidazolyl, thiazolyl, oxazolyl, oxadiazolyl, triazolyl, pyridyl, bipyridyl, pyrimidyl, triazinyl, triazolyl, acridyl, pyridazinyl, pyrazinyl, quinolinyl, quinazolinyl, quinoxalinyl, phenoxazyl, phthalazinyl, pyrido pyrimidinyl, pyrido pyrazinyl, pyrazino pyrazinyl, isoquinolinyl, indolyl, carbazolyl, N-arylcarbazolyl, N-heteroaryl carbazolyl, N-alkyl carbazolyl, benzoxazolyl, benzoimidazolyl, benzothiazolyl, benzocarbazolyl, benzothiophenyl, dibenzothiophenyl, thienothiophenyl, benzofuranyl, phenanthrolinyl, thiazolyl, isooxazolyl, oxadiazolyl, thiadiazolyl, benzothiazolyl, phenothiazinyl, dibenzofuranyl, etc., without limitation.

In the present disclosure, the explanation on the aryl may be applied to the arylene except that arylene is divalent. The explanation on the heteroaryl may be applied to the heteroarylene except that heteroarylene is divalent.

In the present disclosure, the silyl may include alkyl silyl and aryl silyl. Examples of the silyl may include trimethylsilyl, triethylsilyl, t-butyl dimethylsilyl, vinyl dimethylsilyl, propyl dimethylsilyl, triphenylsilyl, diphenylsilyl, phenylsilyl, etc., without limitation.

In the present disclosure, a boron compound may include alkyl boron and aryl boron. Examples of the boron compound may include trimethyl boron, triethyl boron, t-butyl dimethyl boron, triphenyl boron, diphenyl boron, phenyl boron, etc., without limitation.

In the present disclosure, the alkenyl may be linear or branched. The carbon number is not specifically limited, however may be 2 to 30, 2 to 20, or 2 to 10. Examples of the alkenyl may include vinyl, 1-butenyl, 1-pentenyl, 1,3-butadienyl aryl, styrenyl, styrylvinyl, etc., without limitation.

In the present disclosure, the carbon number of the amine is not specifically limited, and may be 1 to 30. The amine may include alkylamine and arylamine. Examples of the amine may include methylamine, dimethylamine, phenylamine, diphenylamine, naphthylamine, 9-methyl-anthracenylamine, triphenylamine, etc., without limitation.

Hereinafter, the polycyclic compound according to an embodiment will be explained.

The polycyclic compound according to an embodiment may be represented by the following Formula 1.

[Formula 1]

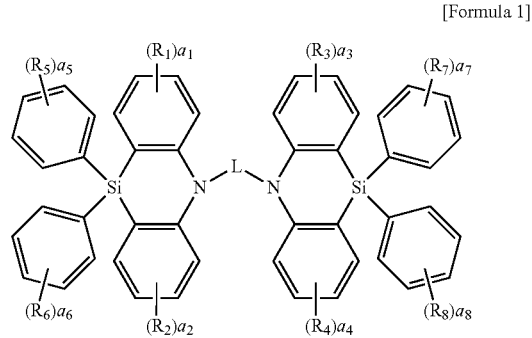

In Formula 1, L may be or may include, e.g., a substituted or unsubstituted arylene group having 6 to 30 ring carbon atoms. In an implementation, L may be or may include, e.g., a substituted or unsubstituted phenylene group. In an implementation, L may be or may include, e.g., a substituted or unsubstituted divalent biphenyl group. In an implementation, L may be or may include, e.g., a substituted or unsubstituted divalent terphenyl group. In an implementation, L may be or may include, e.g., a substituted or unsubstituted fluorenylene group.

In an implementation, L may be or may include, e.g., an unsubstituted phenylene group. In an implementation, L may be or may include, e.g., a mono- or di-substituted phenylene group. In an implementation, L may be or may include, e.g., a phenylene group substituted with at least one of methyl or phenyl. In an implementation, L may be or may include, e.g., a phenylene group substituted with a cyano group.

In an implementation, L may be or may include, e.g., an unsubstituted divalent biphenyl group. In an implementation, L may be or may include, e.g., a di-substituted divalent biphenyl group. In an implementation, L may be or may include, e.g., a divalent biphenyl group substituted with at least one of methyl or phenyl.

In an implementation, L may be or may include, e.g., an unsubstituted divalent terphenyl group. In an implementation, L may be or may include, e.g., a di-substituted fluorenylene group. In an implementation, L may be or may include, e.g., a fluorenylene group substituted with at least one of methyl and phenyl.

$R_1$ to $R_8$ may each independently be or include, e.g., a hydrogen atom, a deuterium atom, a halogen atom, a cyano group, a substituted or unsubstituted silyl group, an alkyl group having 1 to 20 carbon atoms, a substituted or unsubstituted aryl group having 6 to 30 ring carbon atoms, or a substituted or unsubstituted heteroaryl group having 2 to 30 ring carbon atoms. In an implementation, $R_1$ to $R_8$ may each independently be, e.g., a hydrogen atom, a methyl group, a phenyl group, a fluorine atom, or a cyano group.

$a_1$ to $a_4$ may each independently be, e.g., an integer of 0 to 4, and $a_5$ to $a_8$ may each independently be, e.g., an integer of 0 to 5. For example, it would be understood that describing $a_1$ to $a_8$ each being 0 would have the same meaning as $a_1$ to $a_4$ being 4 and $a_5$ to $a_8$ being 5, and $R_1$ to $R_8$ all being hydrogen, it would be understood that describing $a_1$ being 1 and $R_1$ being deuterium would have the same meaning as $a_1$ to $a_4$ being 4 and $a_5$ to $a_8$ being 5, $R_1$ being deuterium, and $R_2$ to $R_8$ all being hydrogen, etc.

In the case where $a_1$ is 2, 3, or 4, the 2, 3, or 4 $R_1$ may be the same or different. In the case where $a_2$ is 2, 3, or 4, the 2, 3, or 4 $R_2$ may be the same or different. In the case where $a_3$ is 2, 3, or 4, the 2, 3, or 4 $R_3$ may be the same or different. In the case where $a_4$ is 2, 3, or 4, the 2, 3, or 4 $R_4$ may be the same or different. In the case where $a_5$ is 2, 3, 4, or 5, the 2, 3, 4, or 5 $R_5$ may be the same or different. In the case where $a_6$ is 2, 3, 4, or 5, the 2, 3, 4, or 5 $R_6$ may be the same or different. In the case where $a_7$ is 2, 3, 4, or 5, the 2, 3, 4, or 5 $R_7$ may be the same or different. In the case where $a_8$ is 2, 3, 4, or 5, the 2, 3, 4, or 5 $R_8$ may be the same or different.

The polycyclic compound represented by Formula 1 may have high lowest triplet energy (T1). In an implementation, the polycyclic compound represented by Formula 1 may have the lowest triplet energy (T1) of, e.g., about 3.2 eV or more. The polycyclic compound represented by Formula 1 may have the lowest triplet energy (T1) of about 3.2 eV or more, when the polycyclic compound represented by Formula 1 is used in a hole transport region, energy transfer of triplet excitons from an emission layer to the hole transport region may be inhibited, and the efficiency of using the triplet excitons may increase, thereby attaining the improvement of device efficiency.

In Formula 1, L may be a group represented by one of the following Formulae 2-1 to 2-8.

[Formula 2-1]

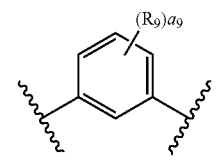

[Formula 2-2]

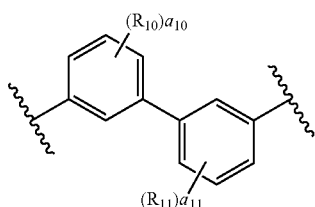

[Formula 2-3]

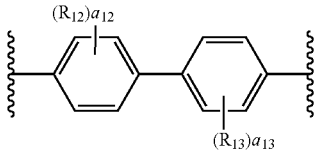

[Formula 2-4]

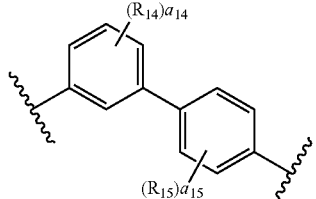

[Formula 2-5]

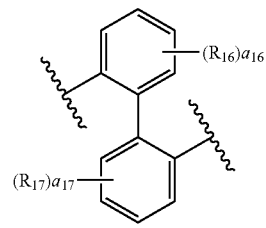

[Formula 2-6]

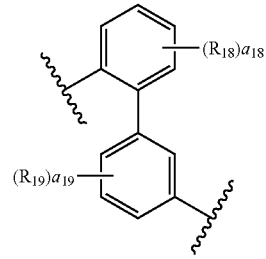

[Formula 2-7]

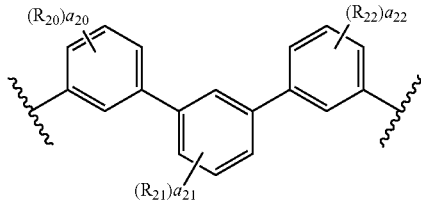

[Formula 2-8]

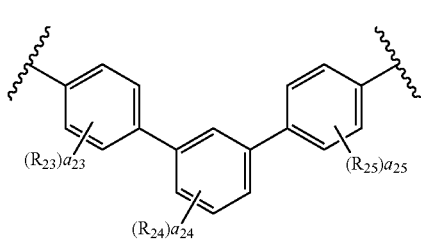

In Formulae 2-1 to 2-8, $R_9$ to $R_{25}$ may each independently be or include, e.g., a hydrogen atom, a deuterium atom, a halogen atom, a cyano group, a substituted or unsubstituted silyl group, an alkyl group having 1 to 20 carbon atoms, a substituted or unsubstituted aryl group having 6 to 30 ring carbon atoms, or a substituted or unsubstituted heteroaryl group having 2 to 30 ring carbon atoms. In an implementation, $R_9$ to $R_{25}$ may be separate or may combine with an adjacent group to form a ring.

$a_9$ to $a_{25}$ may each independently be, e.g., an integer of 0 to 4.

In an implementation, in Formula 2-1, $R_9$ may be, e.g., a hydrogen atom, a methyl group, a phenyl group, a cyano group, or a fluorophenyl group. $a_9$ may be, e.g., an integer of 0 to 4. In the case where $a_9$ is 2, 3, or 4, the 2, 3, or 4 $R_9$ may be the same or different.

In an implementation, in Formula 2-2, $R_{10}$ and $R_{11}$ may each independently be, e.g., a hydrogen atom, a methyl group, or a phenyl group. $a_{10}$ and $a_{11}$ may each independently be, e.g., an integer of 0 to 4. In the case where $a_{10}$ is 2, 3, or 4, the 2, 3, or 4 $R_{10}$ may be the same or different. In the case where $a_{11}$ is 2, 3, or 4, the 2, 3, or 4 $R_{11}$ may be the same or different.

In an implementation, in Formula 2-3, $R_{12}$ and $R_{13}$ may each independently be, e.g., a hydrogen atom, or a methyl group. In an implementation, adjacent $R_{12}$ and $R_{13}$ may combine with each other to form a ring. In the case where both adjacent $a_{10}$ and $a_{11}$ are methyl groups and adjacent $R_{12}$ and $R_{13}$ are combined with each other to form a ring, L may be a substituted or unsubstituted fluorenylene group. $a_{12}$ and $a_{13}$ may each independently be, e.g., an integer of 0 to 4. In the case where $a_{12}$ is 2, 3, or 4, the 2, 3, or 4 $R_{12}$ may be the same or different. In the case where $a_{13}$ is 2, 3, or 4, the 2, 3, or 4 $R_{13}$ may be the same or different.

In an implementation, in Formula 2-4, $R_{14}$ and $R_{15}$ may each independently be, e.g., a hydrogen atom or a methyl group. $a_{14}$ and $a_{15}$ may each independently be, e.g., an integer of 0 to 4. In the case where $a_{14}$ is 2, 3, or 4, the 2, 3, or 4 $R_{14}$ may be the same or different. In the case where $a_{15}$ is 2, 3, or 4, the 2, 3, or 4 $R_{15}$ may be the same or different.

In an implementation, in Formula 2-5, $R_{16}$ and $R_{17}$ may each be, e.g., a hydrogen atom. $a_{16}$ and $a_{17}$ may each independently be, e.g., an integer of 0 to 4. In the case where $a_{16}$ is 2, 3, or 4, the 2, 3, or 4 $R_{16}$ may be the same or different. In the case where $a_{17}$ is 2, 3, or 4, the 2, 3, or 4 $R_{17}$ may be the same or different.

In an implementation, in Formula 2-6, $R_{18}$ and $R_{19}$ may each be, e.g., a hydrogen atom. $a_{18}$ and $a_{19}$ may each independently be, e.g., an integer of 0 to 4. In the case where $a_1$ is 2, 3, or 4, the 2, 3, or 4 $R_{18}$ may be the same or different. In the case where $a_{19}$ is 2, 3, or 4, the 2, 3, or 4 $R_{19}$ may be the same or different.

In an implementation, in Formula 2-7, $R_{20}$ to $R_{22}$ may each be, e.g., a hydrogen atom. $a_{20}$ to $a_{22}$ may each independently be, e.g., an integer of 0 to 4. In the case where $a_{20}$ is 2, 3, or 4, the 2, 3, or 4 $R_{20}$ may be the same or different. In the case where $a_{21}$ is 2, 3, or 4, the 2, 3, or 4 $R_{21}$ may be the same or different. In the case where $a_{22}$ is 2, 3, or 4, the 2, 3, or 4 $R_{22}$ may be the same or different.

In an implementation, in Formula 2-8, $R_{23}$ to $R_{25}$ may each be, e.g., a hydrogen atom. $a_{23}$ to $a_{25}$ may each independently be, e.g., an integer of 0 to 4. In the case where $a_{23}$ is 2, 3, or 4, the 2, 3, or 4 $R_{23}$ may be the same or different. In the case where $a_{24}$ is 2, 3, or 4, the 2, 3, or 4 $R_{24}$ may be the same or different. In the case where $a_{25}$ is 2, 3, or 4, the 2, 3, or 4 $R_{25}$ may be the same or different.

In an implementation, the compound represented by Formula 1 may be a compound represented by the following Formula 3.

[Formula 3]

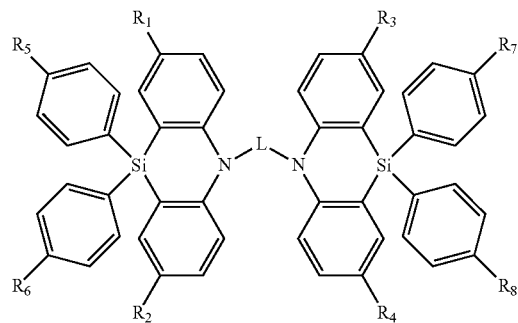

In Formula 3, L may be or may include, e.g., a substituted or unsubstituted arylene group having 6 to 30 ring carbon atoms.

$R_1$ to $R_8$ may each independently be or include, e.g., a hydrogen atom, a deuterium atom, a halogen atom, a cyano group, a substituted or unsubstituted silyl group, an alkyl group having 1 to 20 carbon atoms, a substituted or unsubstituted aryl group having 6 to 30 ring carbon atoms, or a substituted or unsubstituted heteroaryl group having 2 to 30 ring carbon atoms. In an implementation, at least one of $R_1$ to $R_8$ may not be a hydrogen atom. In an implementation, at least one of $R_1$ to $R_8$ may be a deuterium atom, a halogen atom, a cyano group, a substituted or unsubstituted silyl group, an alkyl group having 1 to 20 carbon atoms, a substituted or unsubstituted aryl group having 6 to 30 ring carbon atoms, or a substituted or unsubstituted heteroaryl group having 2 to 30 ring carbon atoms.

In an implementation, $R_1$ to $R_8$ may each independently be, e.g., a hydrogen atom, a methyl group, a phenyl group, a fluorine atom, or a cyano group. In an implementation, at least one of $R_1$ to $R_8$ may not be a hydrogen atom. In an implementation, at least one of $R_1$ to $R_8$ may be, e.g., a methyl group, a phenyl group, a fluorine atom, or a cyano group.

In an implementation, the compound represented by Formula 3 may be a compound represented by Formula 3-1 or 3-2.

[Formula 3-1]

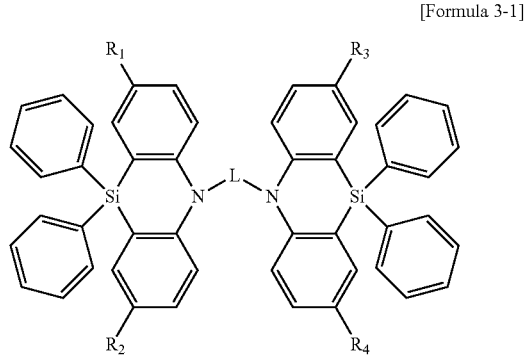

In Formula 3-1, L may be or may include, e.g., a substituted or unsubstituted arylene group having 6 to 30 ring carbon atoms.

$R_1$ to $R_4$ may each independently be or include, e.g., a hydrogen atom, a deuterium atom, a halogen atom, a cyano group, a substituted or unsubstituted silyl group, an alkyl group having 1 to 20 carbon atoms, a substituted or unsubstituted aryl group having 6 to 30 ring carbon atoms, or a substituted or unsubstituted heteroaryl group having 2 to 30 ring carbon atoms. In an implementation, at least one of $R_1$ to $R_4$ may not be a hydrogen atom. In an implementation, at least one of $R_1$ to $R_4$ may be or may include, e.g., a deuterium atom, a halogen atom, a cyano group, a substituted or unsubstituted silyl group, an alkyl group having 1 to 20 carbon atoms, a substituted or unsubstituted aryl group having 6 to 30 ring carbon atoms, or a substituted or unsubstituted heteroaryl group having 2 to 30 ring carbon atoms.

In an implementation, $R_1$ to $R_4$ may each independently be or include, e.g., a hydrogen atom, a methyl group, a phenyl group, a fluorine atom, or a cyano group. In an implementation, at least one of $R_1$ to $R_4$ may not be a hydrogen atom. In an implementation, at least one of $R_1$ to $R_4$ may be, e.g., a methyl group, a phenyl group, a fluorine atom, or a cyano group.

[Formula 3-2]

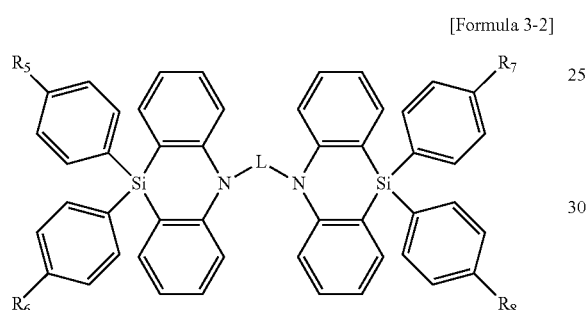

In Formula 3-2, L may be or may include, e.g., a substituted or unsubstituted arylene group having 6 to 30 ring carbon atoms.

$R_5$ to $R_8$ may each independently be or include, e.g., a hydrogen atom, a deuterium atom, a halogen atom, a cyano group, a substituted or unsubstituted silyl group, an alkyl group having 1 to 20 carbon atoms, a substituted or unsubstituted aryl group having 6 to 30 ring carbon atoms, or a substituted or unsubstituted heteroaryl group having 2 to 30 ring carbon atoms. In an implementation, at least one of $R_5$ to $R_8$ may not be a hydrogen atom. In an implementation, least one of $R_5$ to $R_8$ may be or may include, e.g., a deuterium atom, a halogen atom, a cyano group, a substituted or unsubstituted silyl group, an alkyl group having 1 to 20 carbon atoms, a substituted or unsubstituted aryl group having 6 to 30 ring carbon atoms, or a substituted or unsubstituted heteroaryl group having 2 to 30 ring carbon atoms.

In an implementation, $R_5$ to $R_8$ may each independently be or include, e.g., a hydrogen atom, a methyl group, a phenyl group, a fluorine atom, or a cyano group. In an implementation, at least one of $R_5$ to $R_8$ may not be a hydrogen atom. In an implementation, at least one of $R_5$ to $R_8$ may be, e.g., a methyl group, a phenyl group, a fluorine atom, or a cyano group.

In an implementation, the polycyclic compound represented by Formula 1 may be one of the following Compounds 1 to 27.

1

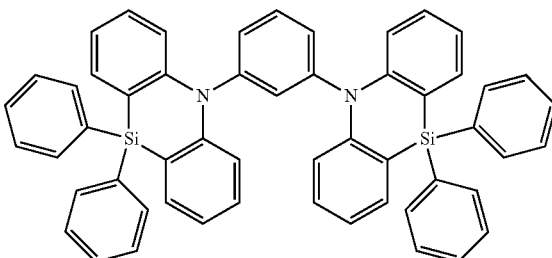

2

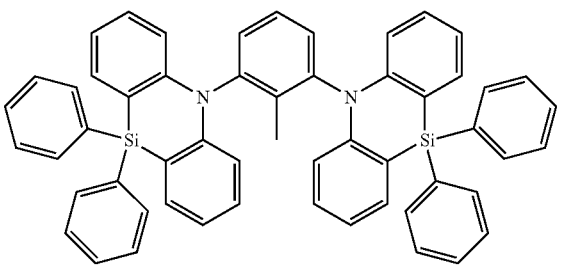

3

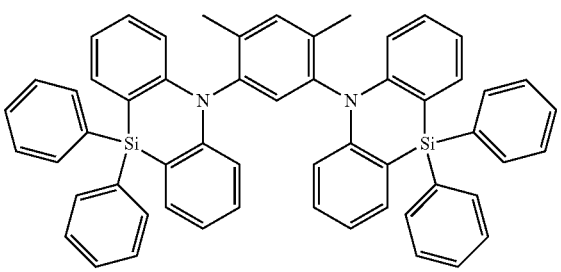

4

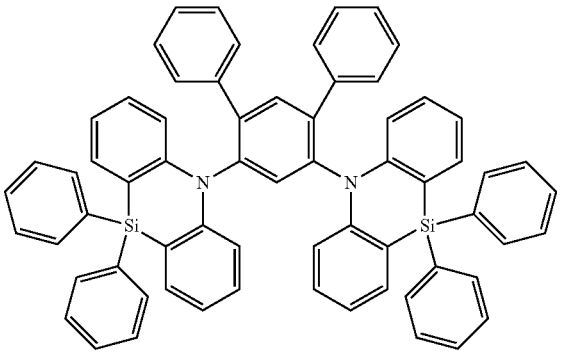

5
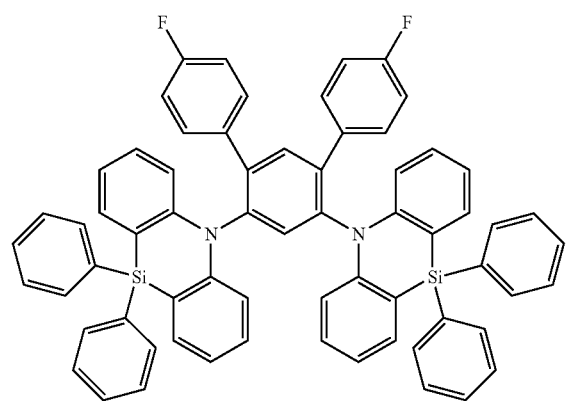
6
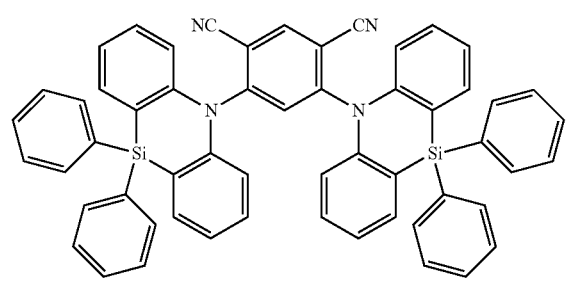
7
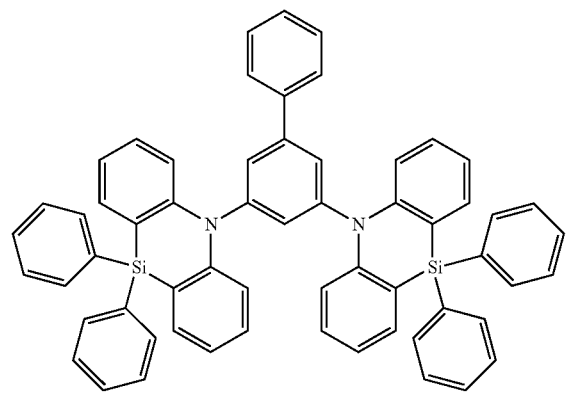
8
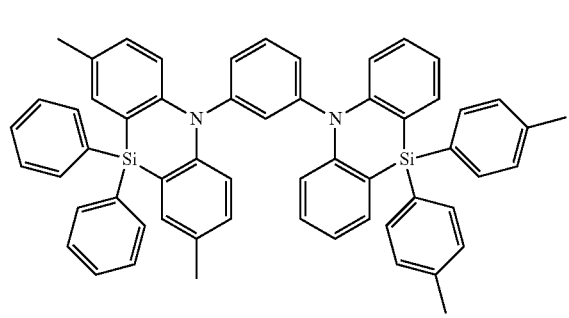
9
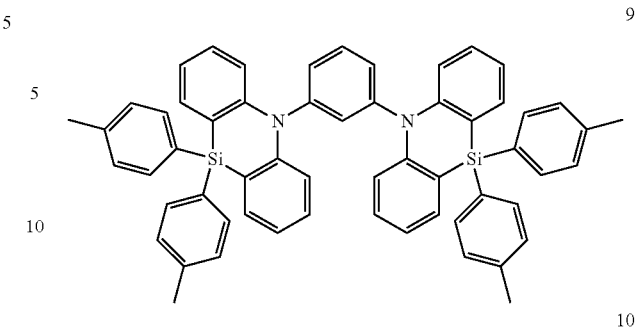
10
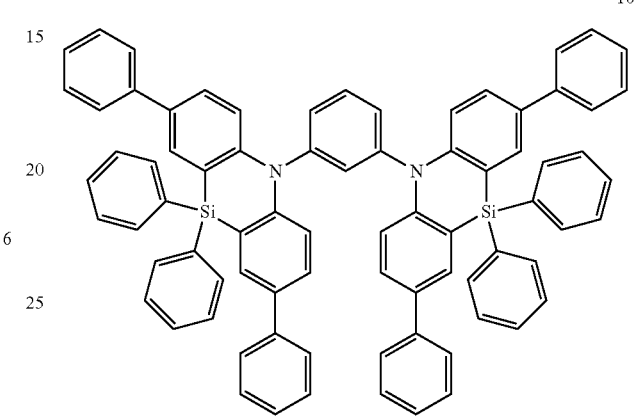
11
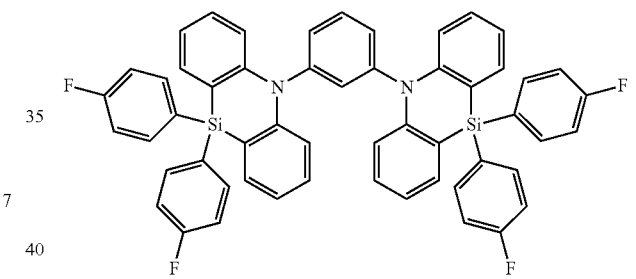
12
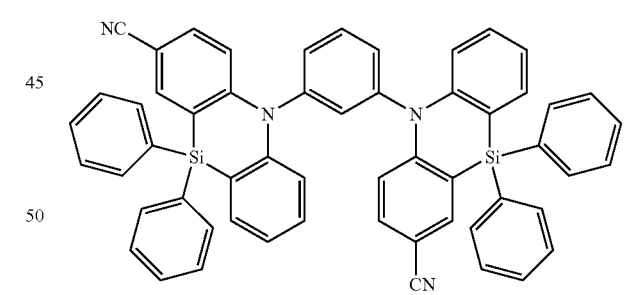
13
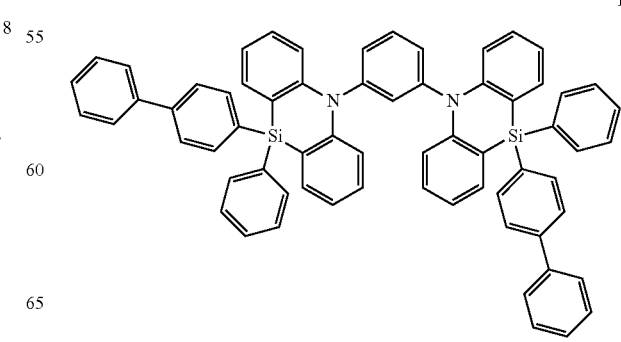

14
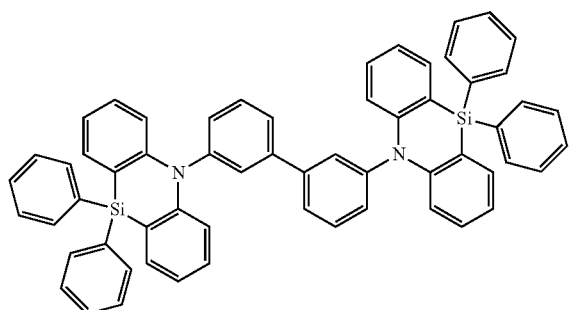
15
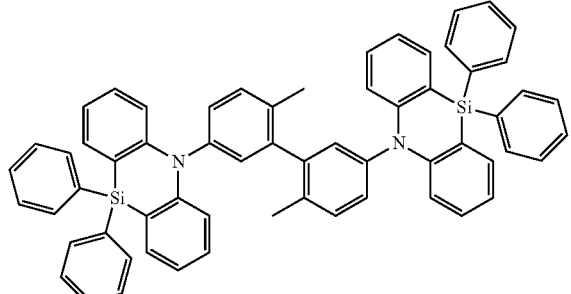
16
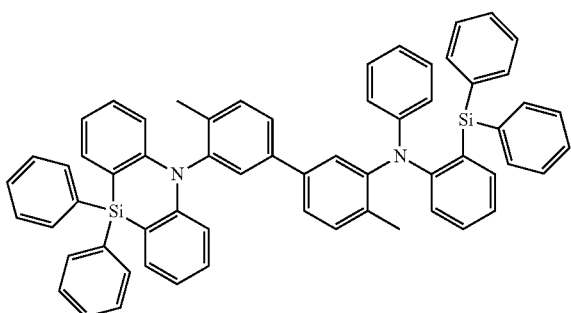
17
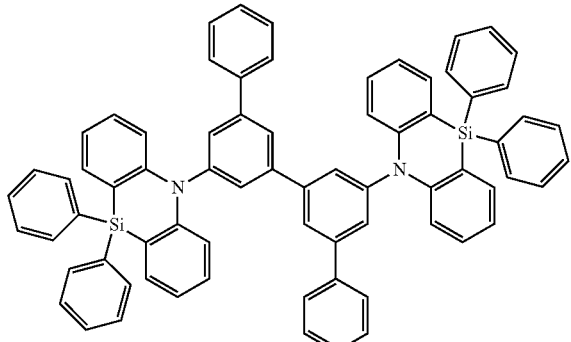
18
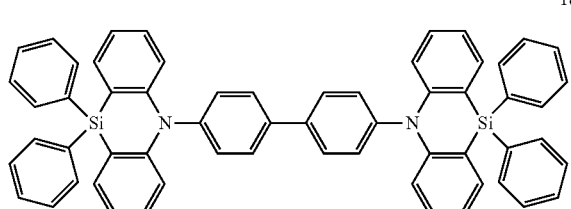
19
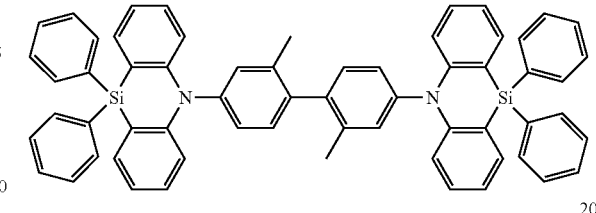
20
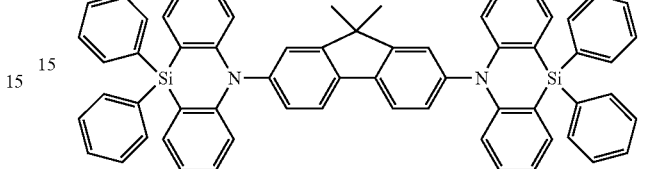
21
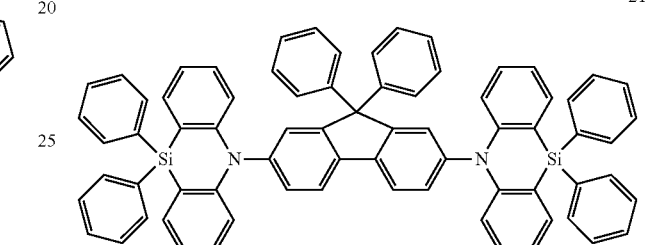
22
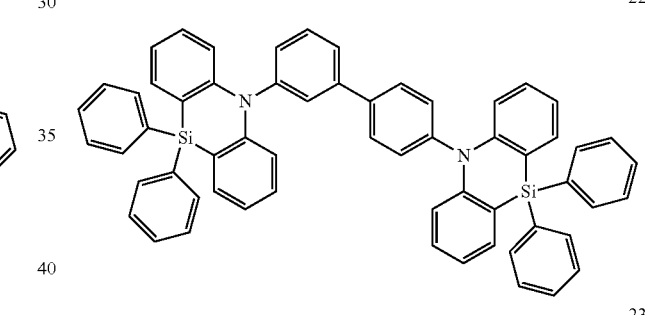
23
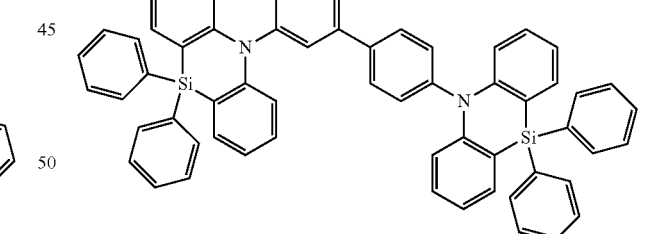
24
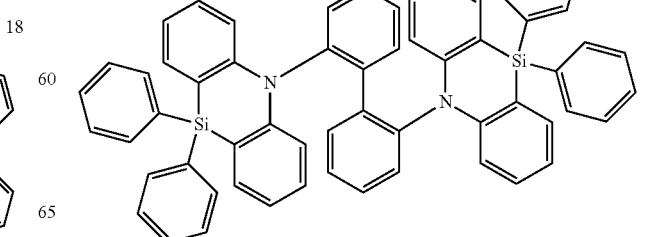

-continued

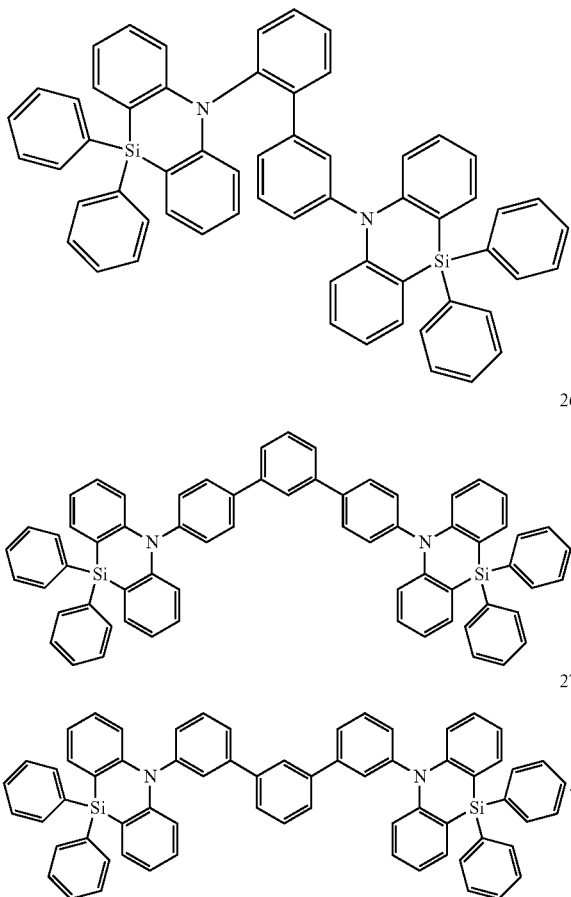

The polycyclic compound according to an embodiment may have a high lowest triplet energy (T1). In the case where the polycyclic compound represented by Formula 1 is applied to an organic electroluminescence device, high emission efficiency and a low driving voltage may be secured. In an implementation, the polycyclic compound represented by Formula 1 may have the lowest triplet energy (T1) of, e.g., about 3.2 eV or more. The polycyclic compound according to an embodiment may be disposed in a hole transport region of an organic electroluminescence device and may help restrain the diffusion of triplet excitons generated in an emission layer to the hole transport region, thereby attaining the high emission efficiency of an organic electroluminescence device.

Hereinafter, an organic electroluminescence device according to an embodiment will be explained. The explanation will be mainly with the difference in the polycyclic compound according to an embodiment, and unexplained part will follow the above-description on the polycyclic compound according to an embodiment.

The organic electroluminescence device according to an embodiment may include the polycyclic compound according to an embodiment. The polycyclic compound according to an embodiment may be a material for thermally activated delayed fluorescence (TADF) or a material for emitting phosphorescence.

Figure 2:
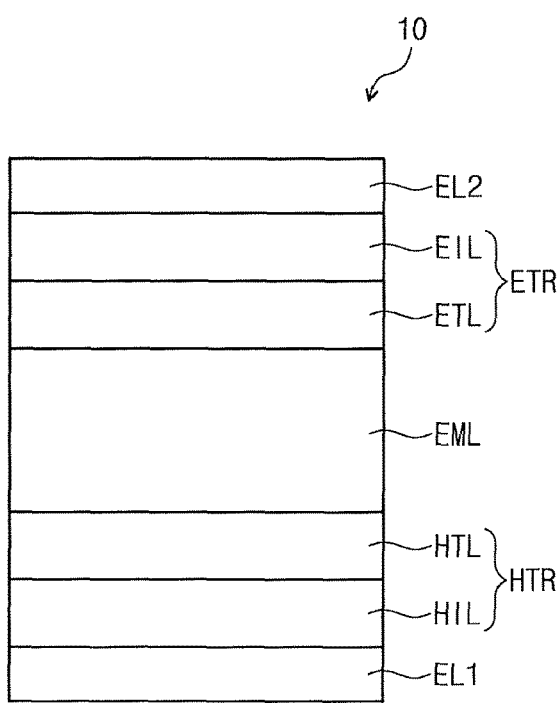
FIG. 2 illustrates a cross-sectional view schematically showing an organic electroluminescence device according to an embodiment.
Figure 3:
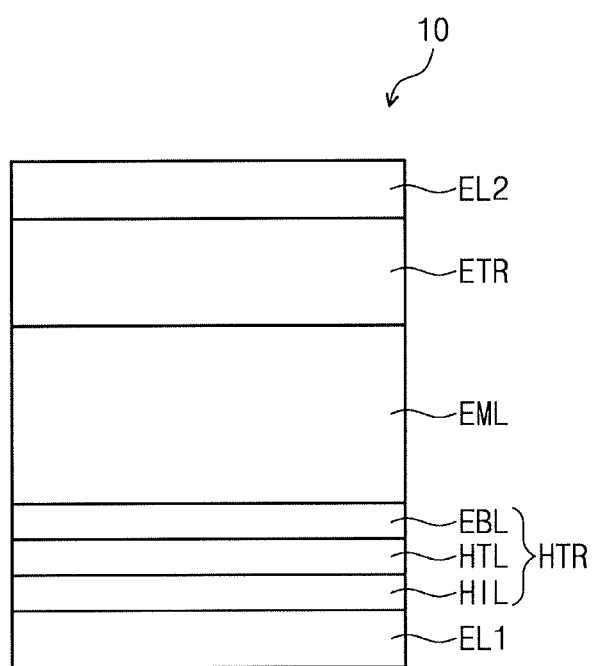
FIG. 3 illustrates a cross-sectional view schematically showing an organic electroluminescence device according to an embodiment.

FIG. 1 illustrates a cross-sectional view schematically showing an organic electroluminescence device according to an embodiment. FIG. 2 illustrates a cross-sectional view schematically showing an organic electroluminescence device according to an embodiment. FIG. 3 illustrates a cross-sectional view schematically showing an organic electroluminescence device according to an embodiment.

Referring to FIGS. 1 to 3, an organic electroluminescence device 10 according to an embodiment may include a first electrode EL1, a hole transport region HTR, an emission layer EML, an electron transport region ETR, and a second electrode EL2.

The first electrode EL1 has conductivity. The first electrode EL1 may be a pixel electrode or an anode. The first electrode EL1 may be a transmissive electrode, a transflective electrode, or a reflective electrode. When the first electrode EL1 is the transmissive electrode, the first electrode EL1 may be formed using a transparent metal oxide, e.g., indium tin oxide (ITO), indium zinc oxide (IZO), zinc oxide (ZnO), or indium tin zinc oxide (ITZO). In the case where the first electrode EL1 is the transflective electrode or reflective electrode, the first electrode EL1 may include, e.g., Ag, Mg, Cu, Al, Pt, Pd, Au, Ni, Nd, Ir, Cr, Li, Ca, LiF/Ca, LiF/Al, Mo, Ti, a compound thereof, or a mixture thereof (e.g., a mixture of Ag and Mg). In an implementation, the first electrode EL1 may include a plurality of layers including the reflective layer or transflective layer formed using the above materials, or a transparent layer formed using ITO, IZO, ZnO, or ITZO.

Hereinafter, a case where the polycyclic compound according an embodiment is included in a hole transport region HTR, will be explained. In an implementation, the polycyclic compound according to an embodiment may be included in at least one organic layer provided between a first electrode EL1 and a second electrode EL2. In an implementation, the polycyclic compound according to an embodiment may be included in an emission layer EML.

An organic electroluminescence device according to an embodiment may include the polycyclic compound according to an embodiment in a hole transport region HTR. For example, the organic electroluminescence device according to an embodiment may include a polycyclic compound represented by Formula 1 in a hole transport region HTR.

[Formula 1]

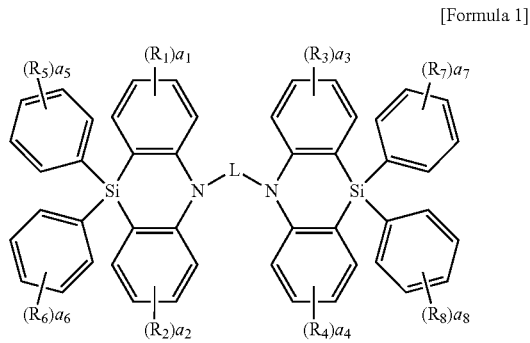

In Formula 1, particular explanation on L, $R_1$ to $R_8$, and $a_1$ to $a_8$ may be the same as described above, and will be omitted.

Particular explanation on the polycyclic compound represented by Formula 1 may be applied as it is, and will be omitted.

The polycyclic compound represented by Formula 1 may have a high lowest triplet energy (T1). In an implementation, the polycyclic compound represented by Formula 1 may have the lowest triplet energy (T1) of, e.g., about 3.2 eV or more.

The hole transport region HTR may be provided on the first electrode EL1. The hole transport region HTR may include at least one of a hole injection layer HIL, a hole transport layer HTL, a hole buffer layer, or an electron blocking layer EBL. The thickness of the hole transport region HTR may be, e.g., from about 1,000 Å to about 1,500 Å.

The hole transport region HTR may have a single layer formed using a single material, a single layer formed using a plurality of different materials, or a multilayer structure including a plurality of layers formed using a plurality of different materials.

For example, the hole transport region HTR may have the structure of a single layer such as a hole injection layer HIL or a hole transport layer HTL, or may have a structure of a single layer formed using a hole injection material and a hole transport material. In an implementation, the hole transport region HTR may have a structure of a single layer formed using a plurality of different materials, or a structure laminated one by one from the first electrode EL1 of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer EBL.

The hole transport region HTR may be formed using various methods such as a vacuum deposition method, a spin coating method, a cast method, a Langmuir-Blodgett (LB) method, an inkjet printing method, a laser printing method, and a laser induced thermal imaging (LITI) method.

The hole transport region HTR may include the polycyclic compound according to an embodiment. The hole transport region HTR may include the polycyclic compound according to an embodiment as a hole transport material.

A layer including the polycyclic compound according to an embodiment may be a layer adjacent to an emission layer EML. In an implementation, in the case where a hole transport layer HTL is adjacent to an emission layer EML in a hole transport region HTR as shown in FIG. 2, the hole transport layer HTL may include the polycyclic compound according to an embodiment. In an implementation, in the case where an electron blocking layer EBL is further included on the hole transport layer HTL in the hole transport region HTR as shown in FIG. 3, the electron blocking layer EBL may include the polycyclic compound according to an embodiment. At least one of the hole transport layer HTL or the electron blocking layer EBL may include one or more kinds of the polycyclic compound represented by Formula 1. The hole transport layer HTL and the electron blocking layer EBL may further include suitable materials in addition to the polycyclic compound represented by Formula 1.

In the case where a hole transport layer HTL or an electron blocking layer EBL includes the polycyclic compound according to an embodiment, the hole injection layer HIL may include, e.g., a phthalocyanine compound such as copper phthalocyanine; N,N'-diphenyl-N,N'-bis-[4-(phenyl-m-tolyl-amino)-phenyl]-biphenyl-4,4'-diamine (DNTPD), 4,4',4''-tris(3-methylphenylphenylamino)triphenylamine (m-MTDATA), 4,4',4''-tris(N,N-diphenylamino)triphenylamine (TDATA), 4,4',4''-tris {N-(2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(naphthalene-1-yl)-N,N'-diphenyl-benzidine (NPB), triphenylamine-containing polyether ketone (TPAPEK), 4-isopropyl-4'-methyldiphenyliodonium tetrakis(pentafluorophenyl)borate, etc.

In the case where a hole transport layer HTL does not include the polycyclic compound according to an embodiment, and an electron blocking layer EBL includes the polycyclic compound according to an embodiment, the hole transport layer HTL may include, e.g., carbazole derivatives such as N-phenyl carbazole, and polyvinyl carbazole, fluorine-based derivatives, N,N'-bis(3-methylphenyl)-N,N'-diphenyl-[1,1-biphenyl]-4,4'-diamine (TPD), triphenylamine-based derivatives such as 4,4',4''-tris(N-carbazolyl) triphenylamine (TCTA), N,N'-di(naphthyl)-N,N'-diphenylbenzidine (NPB), 4,4'-cyclohexylidene bis[N,N-bis (4-methylphenyl)benzenamine] (TAPC), 4,4'-bis[N,N'-(3-tolyl)amino]-3,3'-dimethylbiphenyl (HMTPD), etc.

The thickness of the hole transport region HTR may be from about 100 Å to about 10,000 Å, e.g., from about 100 Å to about 1,000 Å. In the case where the hole transport region HTR includes both the hole injection layer HIL and the hole transport layer HTL, the thickness of the hole injection layer HIL may be from about 100 Å to about 10,000 Å, e.g., from about 100 Å to about 1,000 Å, and the thickness of the hole transport layer HTL may be from about 30 Å to about 1,000 Å. In the case where the thicknesses of the hole transport region HTR, the hole injection layer HIL, and the hole transport layer HTL satisfy the above-described ranges, satisfactory hole transport properties may be attained without the substantial increase of a driving voltage.

The hole transport region HTR may further include a charge generating material in addition to the above-described materials, to improve conductivity. The charge generating material may be dispersed in the hole transport region HTR uniformly or non-uniformly. The charge generating material may be, e.g., a p-dopant. The p-dopant may include one of quinone derivatives, metal oxides, or cyano group-containing compounds, without limitation. Examples of the p-dopant may include quinone derivatives such as tetracyanoquinodimethane (TCNQ), and 2,3,5,6-tetrafluoro-tetracyanoquinodimethane (F4-TCNQ), metal oxides such as tungsten oxide, and molybdenum oxide.

As described above, the hole transport region HTR may further include one of the hole buffer layer or the electron blocking layer EBL in addition to the hole injection layer HIL and the hole transport layer HTL. The hole buffer layer may help compensate an optical resonance distance according to the wavelength of light emitted from the emission layer EML and increase light emission efficiency. Materials included in the hole transport region HTR may be used as materials included in the hole buffer layer. The electron blocking layer EBL is a layer reducing and/or preventing electron injection from the electron transport region ETR to the hole transport region HTR.

The emission layer EML may be provided on the hole transport region HTR. The thickness of the emission layer EML may be, e.g., from about 100 Å to about 300 Å. The emission layer EML may have a single layer formed using a single material, a single layer formed using a plurality of different materials, or a multilayer structure having a plurality of layers formed using a plurality of different materials.

The emission layer EML may emit one of red light, green light, blue light, white light, yellow light, or cyan light. The emission layer EML may include a fluorescent material or a phosphorescent material. The emission layer EML may include a host and a dopant. The emission layer EML may have a thickness of, e.g., about 10 to about 60 nm.

The host may include a suitable host material, e.g., tris(8-hydroxyquinolino)aluminum ($Alq_3$), 4,4'-bis(N-carbazolyl)-1,1'-biphenyl (CBP), poly(n-vinylcarbazole) (PVK), 9,10-di(naphthaline-2-yl)anthracene (ADN), 4,4',4''-tris(carbazol-9-yl)-triphenylamine (TCTA), 1,3,5-tris(N-phenylbenzimidazole-2-yl)benzene (TPBi), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), etc.

The dopant may include, e.g., styryl derivatives (for example, 1,4-bis[2-(3-N-ethylcarbazolyl)vinyl]benzene (BCzVB), 4-(di-p-tolylamino)-4'-[(di-p-tolylamino)styryl] stilbene (DPAVB), N-(4-((E)-2-(6-((E)-4-(diphenylamino) styryl)naphthalen-2-yl)vinyl)phenyl)-N-phenylbenzenamine (N-BDAVBi)), perylene and the derivatives thereof (for example, 2,5,8,11-tetra-t-butylperylene (TBP)), pyrene and the derivatives thereof (for example, 1,1-dipyrene, 1,4-dipyrenylbenzene, 1,4-bis(N,N-diphenylamino)pyrene), etc.

When the emission layer EML emits red light, the emission layer EML may include, e.g., tris(dibenzoylmethanato) phenanthroline europium ($PBD:Eu(DBM)_3(Phen)$), or a fluorescent material including perylene. In the case that the emission layer EML emits red light, the dopant included in the emission layer EML may be selected from a metal complex or an organometallic complex such as bis(1-phenylisoquinoline)acetylacetonate iridium (PIQIr(acac)), bis(1-phenylquinoline)acetylacetonate iridium (PQIr(acac), tris(1-phenylquinoline)iridium (PQIr), and octaethylporphyrin platinum (PtOEP), rubrene and the derivatives thereof, or 4-dicyanomethylene-2-(p-dimethylaminostyryl)-6-methyl-4H-pyran (DCM) and the derivatives thereof.

In the case where the emission layer EML emits green light, the emission layer EML may include a fluorescent material including, e.g., tris(8-hydroxyquinolino)aluminum ($Alq_3$). In the case where the emission layer EML emits green light, the dopant included in the emission layer EML may be selected from a metal complex or organometallic complex such as fac-tris(2-phenylpyridine)iridium (Ir $(ppy)_3$), or coumarin and the derivatives thereof.

In the case where the emission layer EML emits blue light, the emission layer EML may further include a fluorescent material including, e.g., spiro-DPVBi, spiro-6P, distyryl-benzene (DSB), distyryl-arylene (DSA), a polyfluorene (PFO)-based polymer, and a poly(p-phenylene vinylene) (PPV)-based polymer. In the case where the emission layer EML emits blue light, the dopant included in the emission layer EML may be selected from a metal complex or an organometallic complexes such as (4,6-$F_2ppy)_2Irpic$, or perylene and the derivatives thereof.

An electron transport region ETR may be provided on the emission layer EML. The electron transport region ETR may include at least one of an electron blocking layer, an electron transport layer ETL, or an electron injection layer EIL.

The electron transport region ETR may have a single layer formed using a single material, a single layer formed using a plurality of different materials, or a multilayer structure including a plurality of layers formed using a plurality of different materials.

For example, the electron transport region ETR may have the structure of a single layer of an electron injection layer EIL or an electron transport layer ETL, or a single layer structure formed using an electron injection material and an electron transport material. In an implementation, the electron transport region ETR may have a single layer structure formed using a plurality of different materials, or a structure laminated one by one from the first electrode EL1 of electron transport layer ETL/electron injection layer EIL, or hole blocking layer/electron transport layer ETL/electron injection layer EIL. The thickness of the electron transport region ETR may be, e.g., from about 1,000 Å to about 1,500 Å.

The electron transport region ETR may be formed using various methods such as a vacuum deposition method, a spin coating method, a cast method, a Langmuir-Blodgett (LB) method, an inkjet printing method, a laser printing method, and a laser induced thermal imaging (LITI) method.

In the case where the electron transport region ETR includes the electron transport layer ETL, the electron transport region ETR may include, e.g., tris(8-hydroxyquinolinato)aluminum ($Alq_3$), 1,3,5-tri[(3-pyridyl)-phen-3-yl] benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d] imidazol-2-yl)phenyl (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato) aluminum (BAlq), berylliumbis(benzoquinolin-10-olate ($Bebq_2$), 9,10-di(naphthalene-2-yl)anthracene (ADN), or a mixture thereof. The thickness of the electron transport layer ETL may be from about 100 Å to about 1,000 Å, e.g., from about 150 Å to about 500 Å. If the thickness of the electron transport layer ETL satisfies the above-described range, satisfactory electron transport properties may be obtained without the substantial increase of a driving voltage.

In the case where the electron transport region ETR includes the electron injection layer EIL, the electron injection layer EIL may include a metal such as Al, Ag, Li, Mg, and Ca, or a mixture thereof. In an implementation, the electron injection layer EIL may include LiF, lithium quinolate (LiQ), $Li_2O$, BaO, NaCl, CsF, a metal in lanthanoides such as Yb, or a metal halide such as RbCl and RbI. The electron injection layer EIL also may be formed using a mixture material of an electron transport material and an insulating organo metal salt. The organo metal salt may be a material having an energy band gap of about 4 eV or more. In an implementation, the organo metal salt may include, e.g., a metal acetate, a metal benzoate, a metal acetoacetate, a metal acetylacetonate, or a metal stearate. The thickness of the electron injection layer EIL may be from about 1 Å to about 100 Å, e.g., about 3 Å to about 90 Å. In the case where the thickness of the electron injection layer EIL satisfies the above described range, satisfactory electron injection properties may be obtained without inducing the substantial increase of a driving voltage.

The electron transport region ETR may include a hole blocking layer, as described above. The hole blocking layer may include, e.g., at least one of 2,9-dimethyl-4,7-diphenyl-1,10-phenanthroline (BCP), or 4,7-diphenyl-1,10-phenanthroline (Bphen).

The second electrode EL2 may be provided on the electron transport region ETR. The second electrode EL2 may be a common electrode or a cathode. The second electrode EL2 may be a transmissive electrode, a transflective electrode or a reflective electrode. In the case where the second electrode EL2 is the transmissive electrode, the second electrode EL2 may include a transparent metal oxide, e.g., ITO, IZO, ZnO, ITZO, etc.

In the case where the second electrode EL2 is the transflective electrode or reflective electrode, the second electrode EL2 may include, e.g., Ag, Mg, Cu, Al, Pt, Pd, Au, Ni, Nd, Ir, Cr, Li, Ca, LiF/Ca, LiF/Al, Mo, Ti, a compound thereof, or a mixture thereof (e.g., a mixture of Ag and Mg). The second electrode EL2 may have a multilayered structure including a reflective layer or a transflective layer formed using the above-described materials, and a transparent conductive layer formed using ITO, IZO, ZnO, ITZO, etc.

In an implementation, the second electrode EL2 may be connected with an auxiliary electrode. If the second electrode EL2 is connected with the auxiliary electrode, the resistance of the second electrode EL2 may decrease.

In the organic electroluminescence device 10, a voltage may be applied to each of the first electrode EL1 and the second electrode EL2, and holes injected from the first electrode EL1 move via the hole transport region HTR to the emission layer EML, and electrons injected from the second electrode EL2 move via the electron transport region ETR to the emission layer EML. The electrons and holes are recombined in the emission layer EML to generate excitons, which may emit light via transition from an excited state to a ground state.

In the case where the organic electroluminescence device 10 is a top emission type, the first electrode EL1 may be the reflective electrode, and the second electrode EL2 may be the transmissive electrode or transflective electrode. In the case where the organic electroluminescence device 10 is a bottom emission type, the first electrode EL1 may be the transmissive electrode or the transflective electrode, and the second electrode EL2 may be the reflective electrode.

The organic electroluminescence device according to an embodiment may include the polycyclic compound represented by Formula 1, and attains high emission efficiency and a low driving voltage. The polycyclic compound represented by Formula 1 may have high lowest triplet energy (T1). In an implementation, the polycyclic compound represented by Formula 1 may have the lowest triplet energy (T1) of about 3.2 eV or more. The polycyclic compound according to an embodiment may be disposed in a hole transport region HTR and may help restrain the diffusion of triplet excitons generated in an emission layer EML toward a hole transport region HTR, thereby securing high emission efficiency.

The polycyclic compound according to an embodiment may be synthesized, for example, as follows.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Synthetic Examples

1. Synthesis of Compound 1

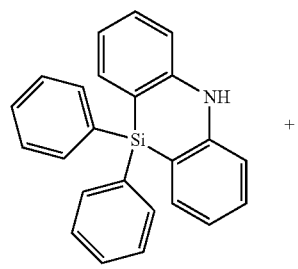

+

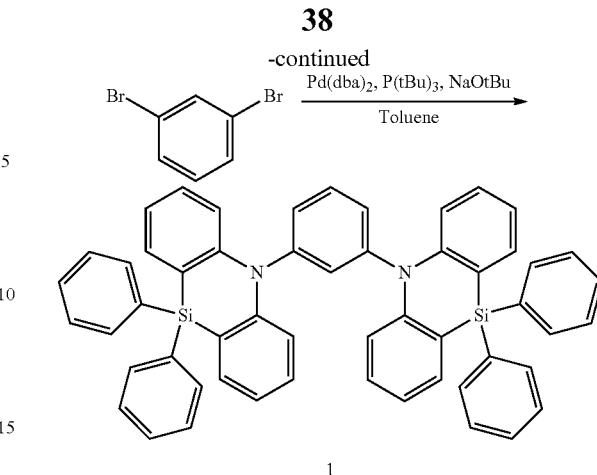

Under an Ar atmosphere, 1.49 g of 1,3-dibromobenzene, 0.18 g of bis(dibenzylideneacetone)palladium(0), and 7.42 g of sodium tert-butoxide, 100 ml of toluene, and 1.0 ml of a 2 M toluene solution of tri(tert-butyl)phosphine were added one by one to 4.50 g of 10,10-diphenyl-phenazasiline, followed by heating and refluxing for 5 hours. The reaction solution thus obtained was cooled to ambient temperature and filtered, and 100 ml of ethanol was added to a filtrate. Precipitated crystals were filtered and washed with 50 ml of water, and 100 ml of ethanol one by one to obtain 4.4 g (yield 94%) of Compound 1 as a lemon yellow powder. The chemical shift values of the compound measured by $^1$H NMR were 7.88 (t, 1H), 7.56-7.61 (m, 12H), 7.37-7.39 (m, 2H), 7.26-7.32 (m, 12H), 7.21-7.24 (m, 5H), 6.95 (dt, 4H), 6.60 (dd, 4H). In addition, the molecular weight of Compound 1 measured by FAB-MS was 772. From the results, the lemon yellow powder compound was identified as Compound 1.

2. Synthesis of Compound 3

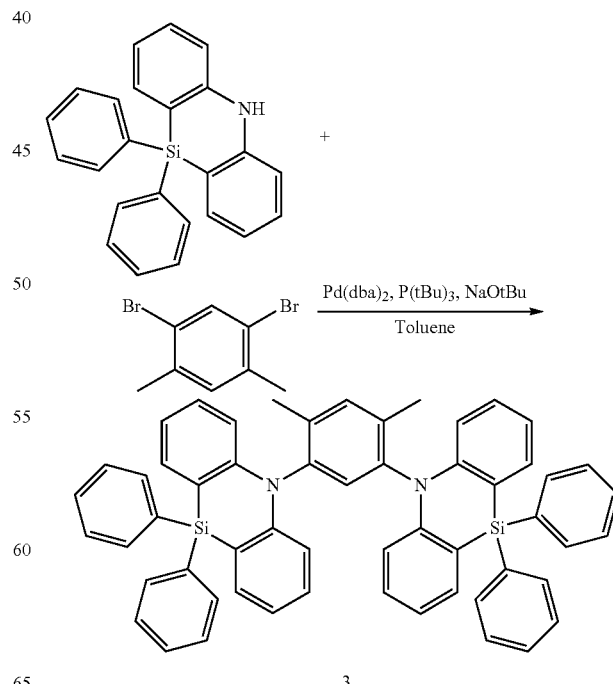

Under an Ar atmosphere, 1.49 g of 4,6-dibromo-m-xylene, 0.18 g of bis(dibenzylideneacetone)palladium(0), and 7.42 g of sodium tert-butoxide, 100 ml of toluene, and 1.0 ml of a 2 M toluene solution of tri(tert-butyl)phosphine were added one by one to 4.50 g of 10,10-diphenyl-phenazasiline, followed by heating and refluxing for 5 hours. The reaction solution thus obtained was cooled to ambient temperature and filtered, and 100 ml of ethanol was added to a filtrate. Precipitated crystals were filtered and washed with 50 ml of water, and 100 ml of ethanol one by one to obtain 3.44 g (yield 68%) of Compound 3 as a lemon yellow powder. The molecular weight of Compound 3 measured by FAB-MS was 800. From the results, the lemon yellow powder compound was identified as Compound 3.

3. Synthesis of Compound 14

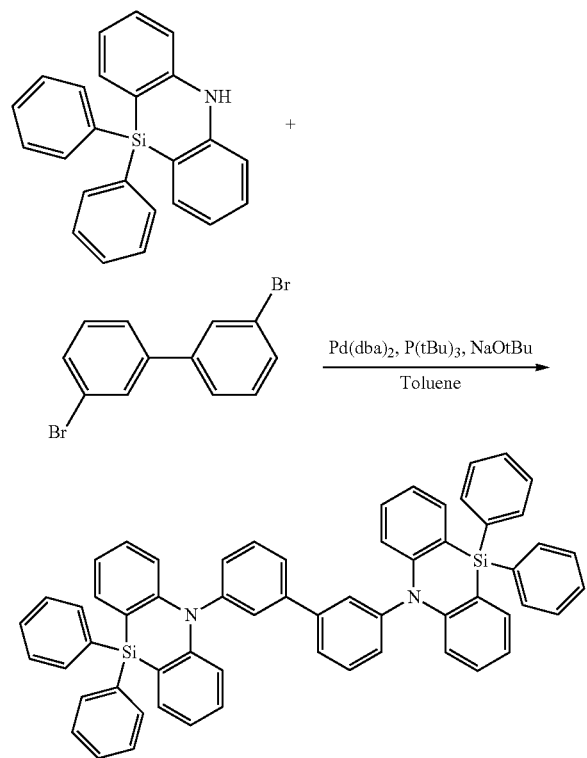

Under an Ar atmosphere, 1.49 g of 3,3''-dibromobiphenyl, 0.18 g of bis(dibenzylideneacetone)palladium(0), and 7.42 g of sodium tert-butoxide, 100 ml of toluene, and 1.0 ml of a 2 M toluene solution of tri(tert-butyl)phosphine were added one by one to 4.50 g of 10,10-diphenyl-phenazasiline, followed by heating and refluxing for 5 hours. The reaction solution thus obtained was cooled to ambient temperature and filtered, and 100 ml of ethanol was added to a filtrate. Precipitated crystals were filtered, washed with 50 ml of water, and 100 ml of ethanol one by one and separated by column chromatography (toluene) to obtain 4.90 g (yield 92%) of Compound 14 as a lemon yellow powder. The molecular weight of Compound 14 measured by FAB-MS was 848. From the results, the lemon yellow powder compound was identified as Compound 14.

4. Synthesis of Compound 15

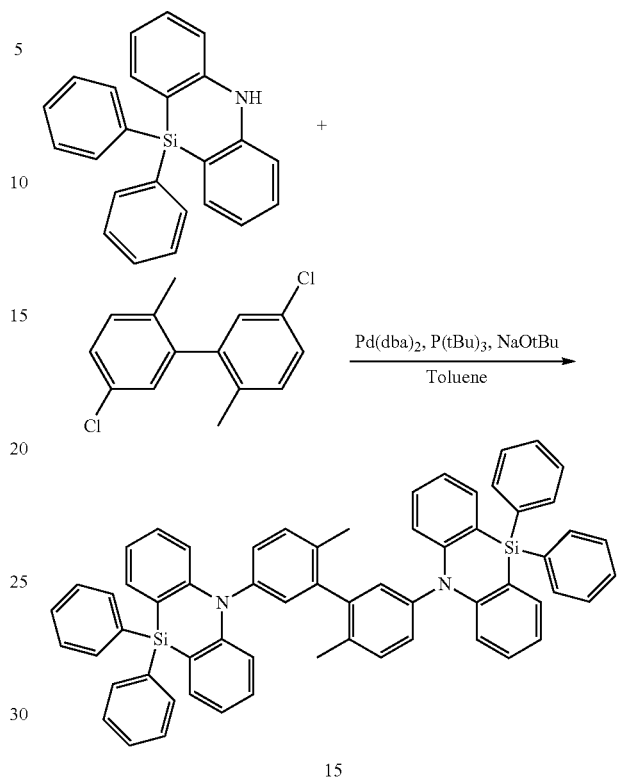

Under an Ar atmosphere, 1.58 g of 2,2''-dimethyl-4,4''-dichlorobiphenyl, 0.18 g of bis(dibenzylideneacetone)palladium(0), and 7.42 g of sodium tert-butoxide, 100 ml of toluene, and 1.0 ml of a 2 M toluene solution of tri(tert-butyl)phosphine were added one by one to 4.50 g of 10,10-diphenyl-phenazasiline, followed by heating and refluxing for 5 hours. The reaction solution thus obtained was cooled to ambient temperature and filtered, and 100 ml of ethanol was added to a filtrate. Precipitated crystals were filtered, washed with 50 ml of water, and 100 ml of ethanol one by one, and separated by column chromatography (toluene) to obtain 4.80 g (yield 87%) of Compound 15 as a lemon yellow powder. The molecular weight of Compound 15 measured by FAB-MS was 876. From the results, the lemon yellow powder compound was identified as Compound 15.

(Device Manufacturing Examples)

Organic electroluminescence devices of Examples 1 to 4 were manufactured using Compounds 1, 3, 14, and 15, respectively as materials for an electron blocking layer.

[Example Compounds]

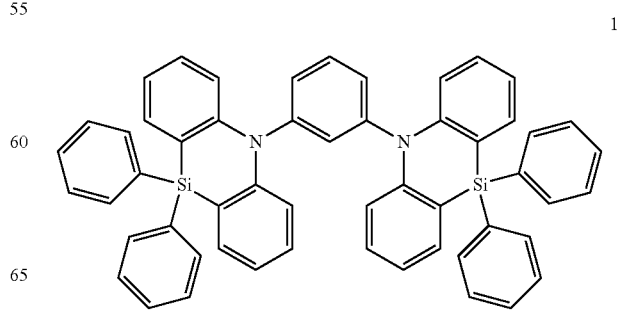

1

3

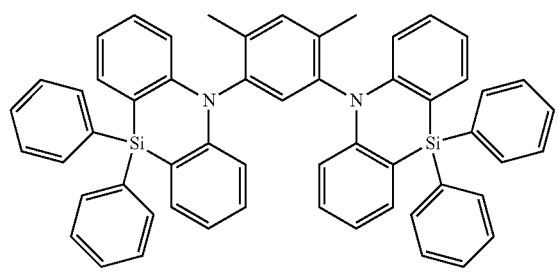

14

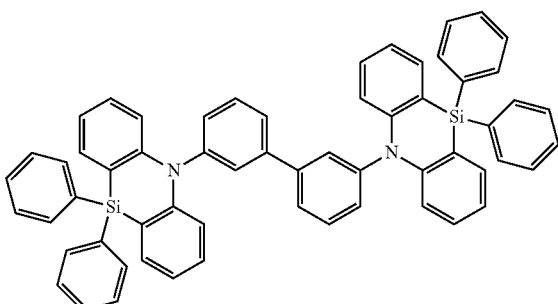

15

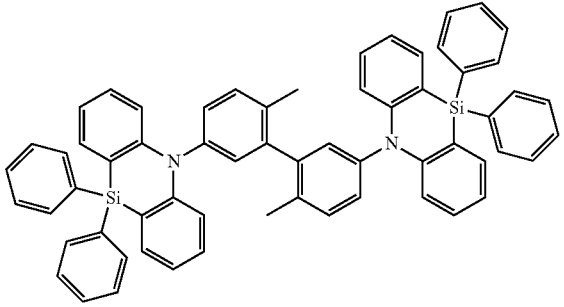

Organic electroluminescence devices of Comparative Examples 1 to 5 were manufactured using the following Comparative Compounds X-1 to X-5, respectively, as materials for an electron blocking layer.

[Comparative Compounds]

X-1

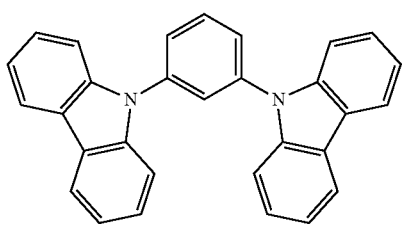

X-2

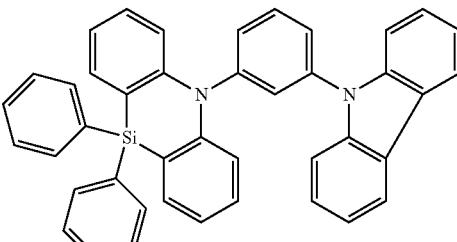

X-3

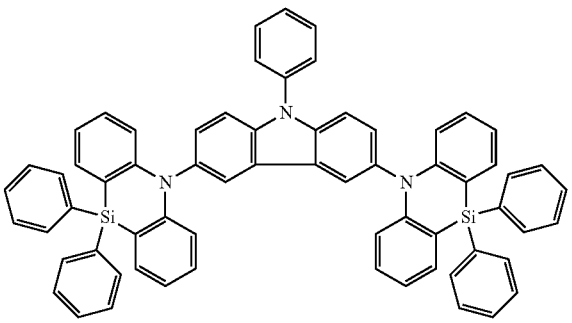

X-4

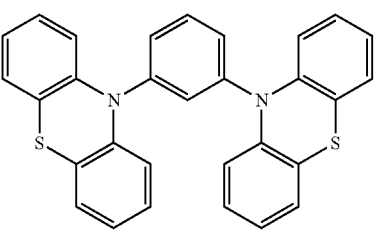

X-5

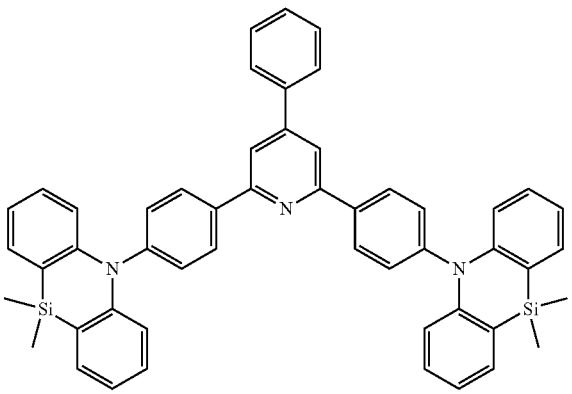

The organic electroluminescence devices of Examples 1 to 4 and Comparative Examples 1 to 5 were manufactured as follows. A first electrode was formed using ITO and having a thickness of about 150 nm, a hole injection layer was formed using dipyrazino[2,3-f: 2',3'-h] quinoxaline-2, 3,6,7,10,11-hexacarbonitrile (HAT-CN) and having a thickness of about 10 nm, a hole transport layer was formed using 4,4'-bis[N-(1-naphthyl)-N-phenyl-amino] biphenyl (α-NPB) and having a thickness of about 80 nm, an electron blocking layer was formed using the example compound or the comparative compound and having a thickness of about 5 nm, an emission layer was formed using bis{2-[di(phenyl)phosphino]phenyl}ether oxide (DPEPO) doped with 18% 10-phenyl-10H,10'H-spiro[acridine-9,9'-anthracen]-10'-one (ACRSA) and having a thickness of about 20 nm, a hole blocking layer was formed using DPEPO and having a thickness of about 10 nm, an electron transport layer was formed using 1,3,5-tris(1-phenyl-1H-benzimidazol-2-yl)benzene (TPBi) and having a thickness of about 30 nm, an electron injection layer was formed using lithium fluoride (LiF) and having a thickness of about 0.5 nm, and a second electrode was formed using Al and having a thickness of about 100 nm. Each layer was formed by a deposition method in vacuum.

After that, the driving voltage and external quantum efficiency of the organic electroluminescence devices thus manufactured were evaluated. The evaluation results are shown in Table 1 below. The driving voltage in each Example or Comparative Example is a measured value at a current density of 10 mA/cm$^2$.

TABLE 1

| | Electron blocking layer | Driving voltage (V) | External quantum efficiency (%) |
|---|---|---|---|
| Example 1 | Example Compound 1 | 6.3 | 18.1 |
| Example 2 | Example Compound 3 | 6.6 | 18.5 |
| Example 3 | Example Compound 14 | 6.1 | 16.7 |
| Example 4 | Example Compound 15 | 6.5 | 18.1 |
| Comparative Example 1 | Comparative Compound X-1 | 6.6 | 15.0 |
| Comparative Example 2 | Comparative Compound X-2 | 6.6 | 14.8 |
| Comparative Example 3 | Comparative Compound X-3 | 6.4 | 12.0 |
| Comparative Example 4 | Comparative Compound X-4 | 6.4 | 10.6 |
| Comparative Example 5 | Comparative Compound X-5 | 7 | 7.9 |

Referring to the results in Table 1, it may be seen that organic electroluminescence devices according to Examples 1 to 4 exhibited a decreased driving voltage and improved external quantum efficiency, when compared to those according to Comparative Examples 1 to 4.

In particular, when comparing Example 1 with Comparative Examples 1 to 5, the organic electroluminescence device according to Example 1 had a driving voltage that was about 0.1 V to about 0.7 V lower, and an external quantum efficiency that was about 3.1% to about 10.2% greater, when compared to those of the Comparative Examples. When comparing Example 2 with Comparative Examples 1 to 5, the organic electroluminescence device according to Example 2 exhibited an external quantum efficiency that was about 3.5% to about 10.6% greater, when compared to that of the Comparative Examples. When comparing Example 3 with Comparative Examples 1 to 5, the organic electroluminescence device according to Example 3 had a driving voltage that was about 0.3 V to about 0.9 V lower, and an external quantum efficiency that was about 1.7% to about 8.8% greater, when compared to those of the Comparative Examples. When comparing Example 4 with Comparative Examples 1 to 5, the organic electroluminescence device according to Example 4 had an external quantum efficiency that was about 3.1% to about 10.2% greater, when compared to that of the Comparative Examples.

From the results, it may be seen that an organic electroluminescence device according to an embodiment may attain a decreased driving voltage and high emission efficiency.

By way of summation and review, for the application of an organic electroluminescence device to a display, the organic electroluminescence device may have a decreased driving voltage and increased emission efficiency.

The embodiments may provide a polycyclic compound used in an organic electroluminescence device having high emission efficiency.

The embodiments may provide an organic electroluminescence device having high emission efficiency.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A polycyclic compound represented by the following Formula 1:

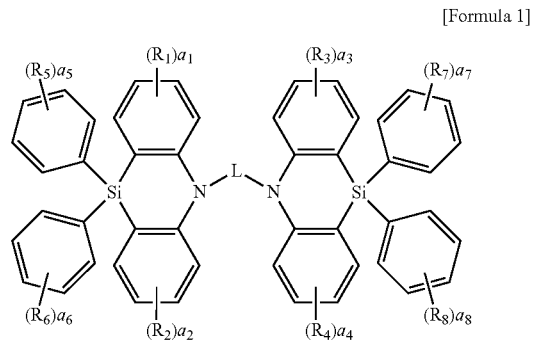

[Formula 1]

wherein, in Formula 1,

L is a substituted or unsubstituted phenylene group, a substituted or unsubstituted divalent biphenyl group, a substituted or unsubstituted divalent terphenyl group, or a substituted or unsubstituted fluorenylene group, $R_1$ to $R_8$ are each independently a hydrogen atom, a deuterium atom, a halogen atom, a cyano group, a substituted or unsubstituted silyl group, an alkyl group having 1 to 20 carbon atoms, a substituted or unsubstituted aryl group having 6 to 30 ring carbon atoms, or a substituted or unsubstituted heteroaryl group having 2 to 30 ring carbon atoms, $a_1$ to $a_4$ are each independently an integer of 0 to 4, and $a_5$ to $a_8$ are each independently an integer of 0 to 5.

2. The polycyclic compound as claimed in claim 1, wherein L is a group represented by one of the following Formulae 2-1 to 2-8:

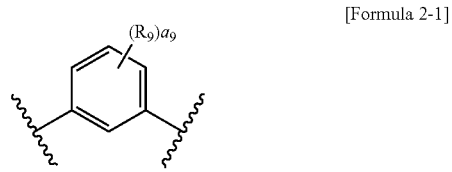

[Formula 2-1]

-continued

[Formula 2-2]
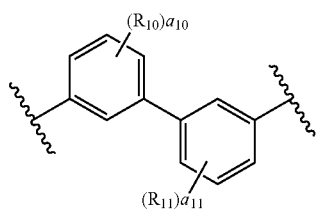

[Formula 2-3]
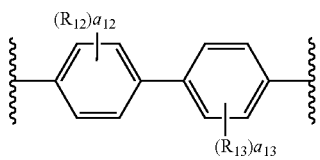

[Formula 2-4]
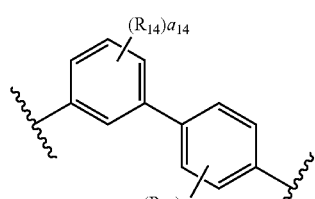

[Formula 2-5]
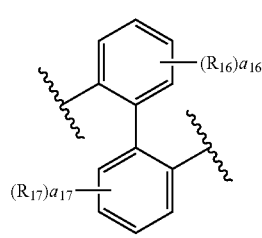

[Formula 2-6]
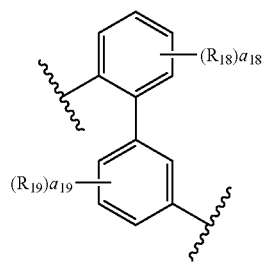

[Formula 2-7]
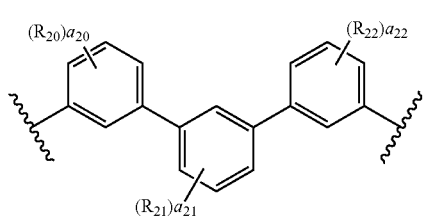

[Formula 2-8]
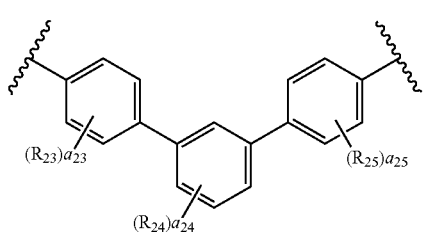

wherein, in Formulae 2-1 to 2-8, $R_9$ to $R_{25}$ are each independently a hydrogen atom, a deuterium atom, a halogen atom, a cyano group, a substituted or unsubstituted silyl group, an alkyl group having 1 to 20 carbon atoms, a substituted or unsubstituted aryl group having 6 to 30 ring carbon atoms, or a substituted or unsubstituted heteroaryl group having 2 to 30 ring carbon atoms, $R_9$ to $R_{25}$ are separate or combine with an adjacent group to form a ring, and $a_9$ to $a_{25}$ are each independently an integer of 0 to 4.

3. The polycyclic compound as claimed in claim 1, wherein the polycyclic compound represented by Formula 1 is represented by the following Formula 3:

[Formula 3]
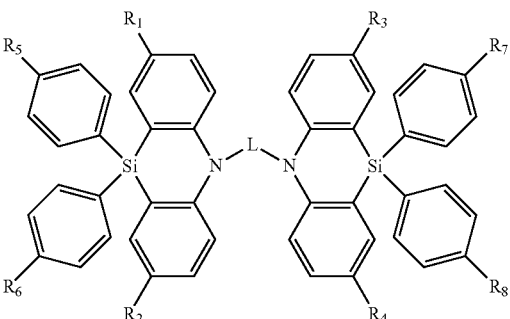

wherein, in Formula 3,

L is a substituted or unsubstituted phenylene group, a substituted or unsubstituted divalent biphenyl group, a substituted or unsubstituted divalent terphenyl group, or a substituted or unsubstituted fluorenylene group, $R_1$ to $R_8$ are each independently a hydrogen atom, a deuterium atom, a halogen atom, a cyano group, a substituted or unsubstituted silyl group, an alkyl group having 1 to 20 carbon atoms, a substituted or unsubstituted aryl group having 6 to 30 ring carbon atoms, or a substituted or unsubstituted heteroaryl group having 2 to 30 ring carbon atoms, and at least one of $R_1$ to $R_8$ is a deuterium atom, a halogen atom, a cyano group, a substituted or unsubstituted silyl group, an alkyl group having 1 to 20 carbon atoms, a substituted or unsubstituted aryl group having 6 to 30 ring carbon atoms, or a substituted or unsubstituted heteroaryl group having 2 to 30 ring carbon atoms.

4. The polycyclic compound as claimed in claim 1, wherein:

$R_1$ to $R_8$ are each independently a hydrogen atom, a methyl group, a phenyl group, a fluorine atom, or a cyano group, and at least one of $R_1$ to $R_8$ is a methyl group, a phenyl group, a fluorine atom, or a cyano group.

5. The polycyclic compound as claimed in claim 1, wherein the polycyclic compound represented by Formula 1 is one the following Compounds 1 to 27:

1
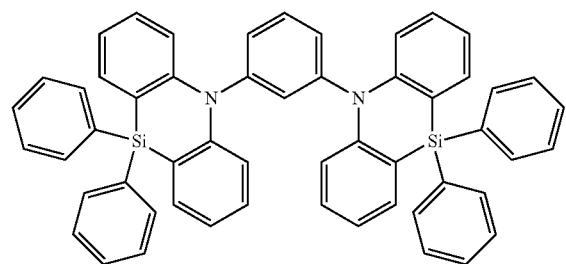
2
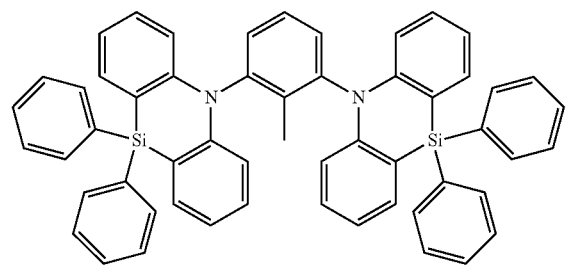
3
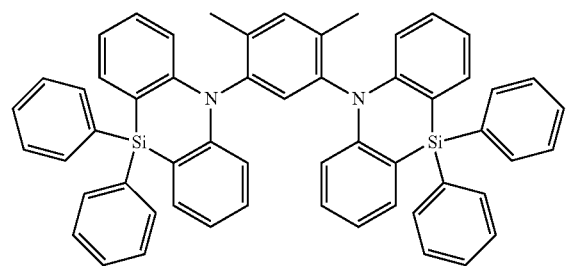
4
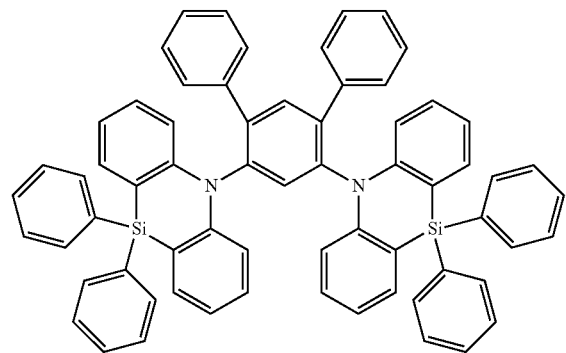
5
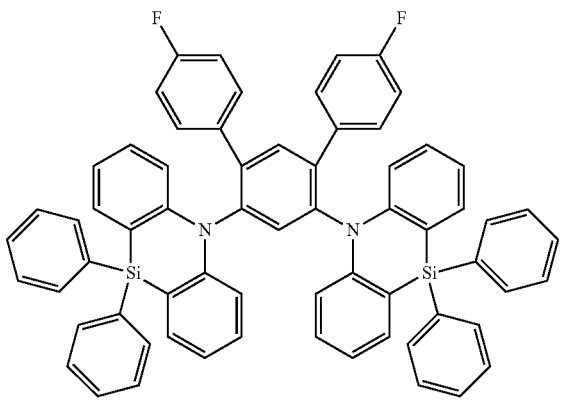
6
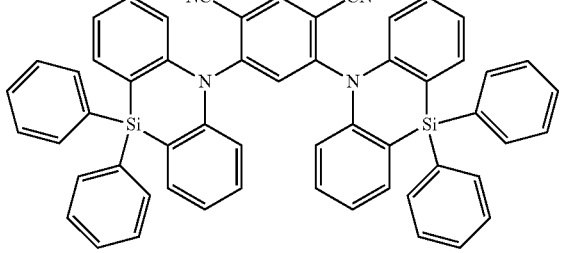
7
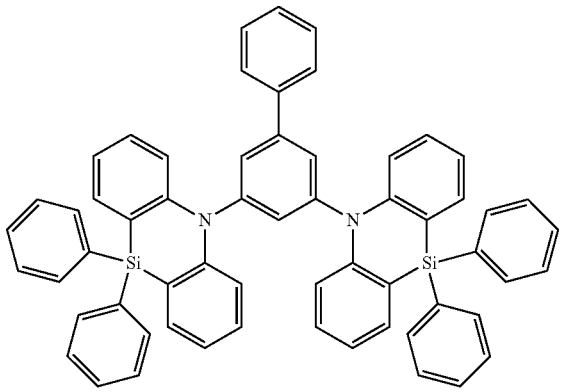
8
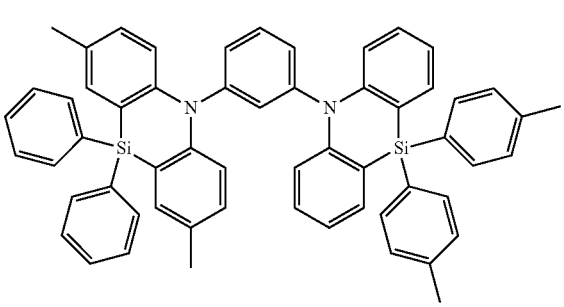

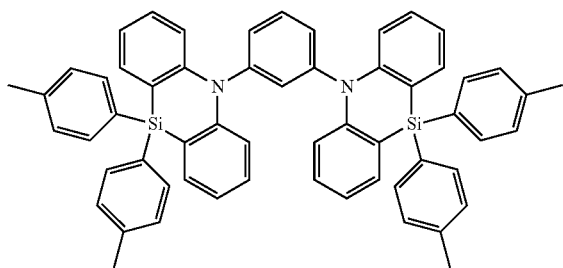
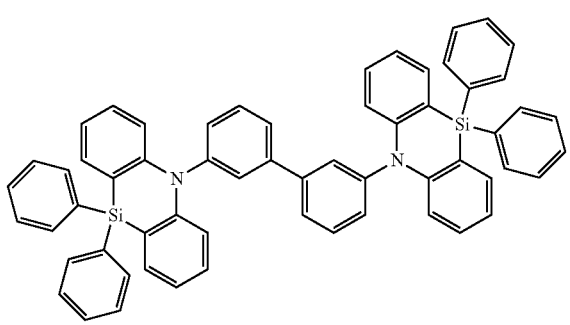
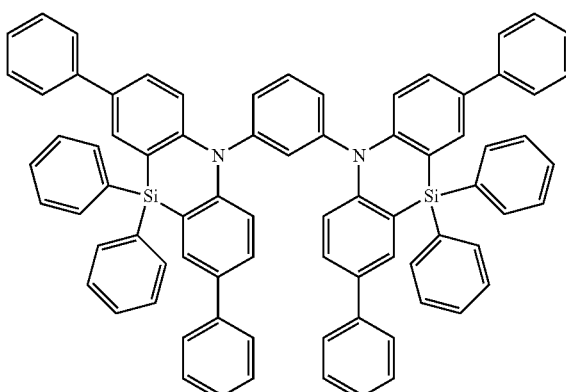
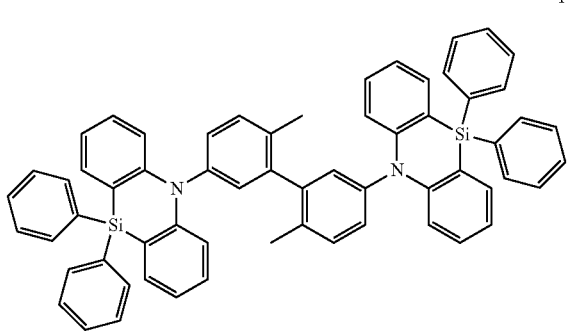
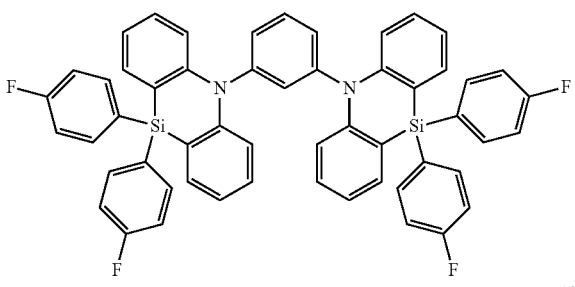
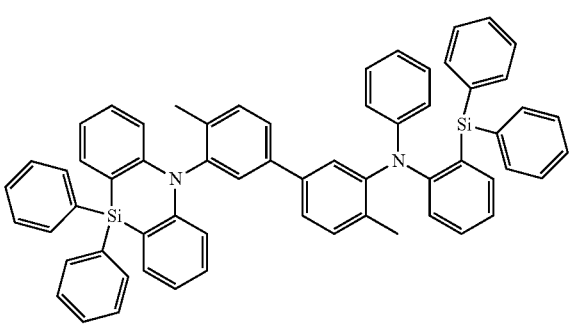
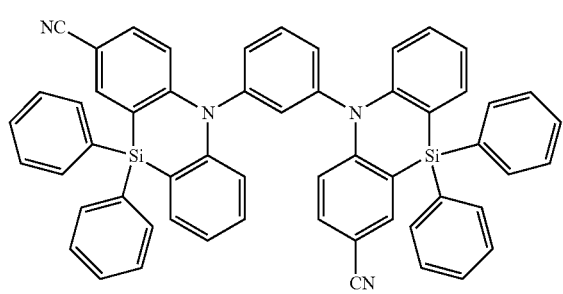
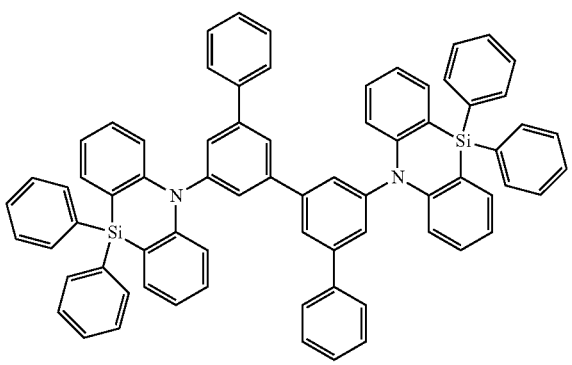
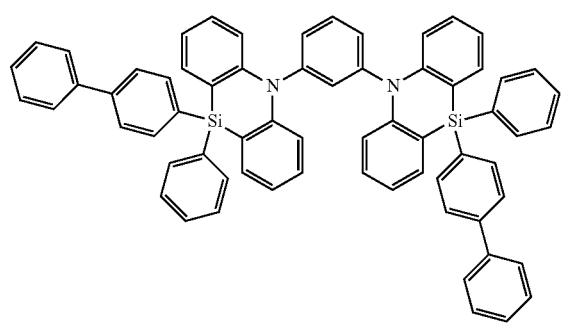
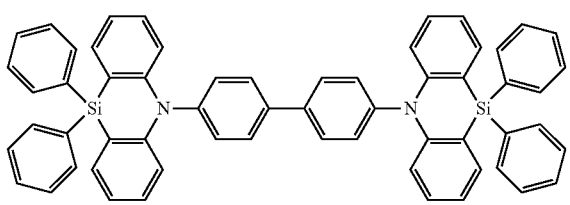

19

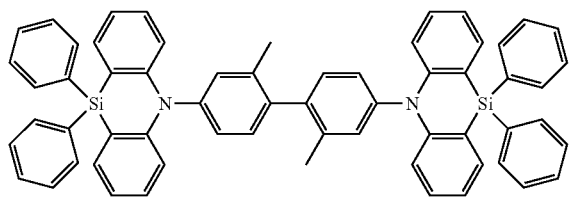

20

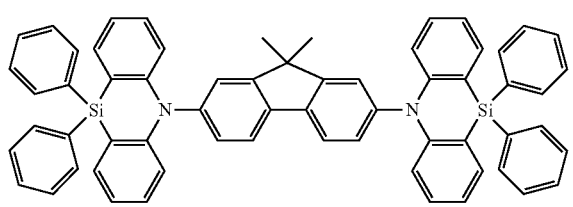

21

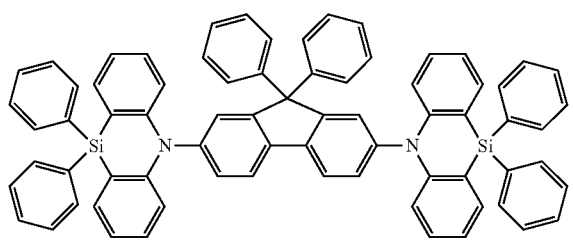

22

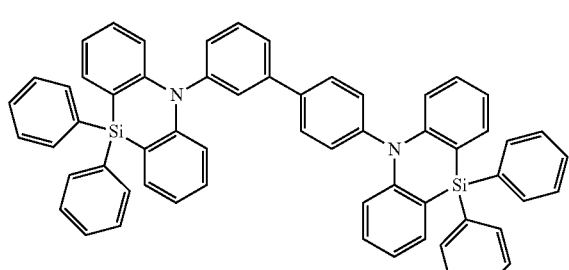

23

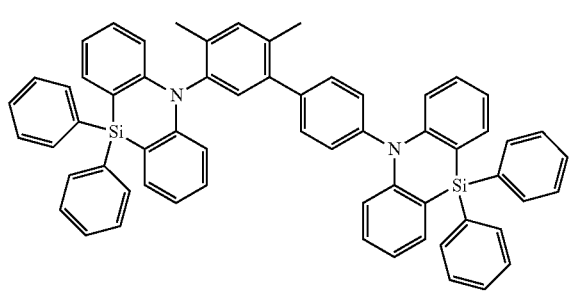

24

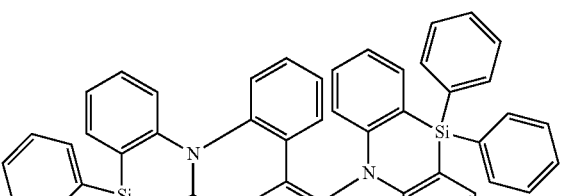

25

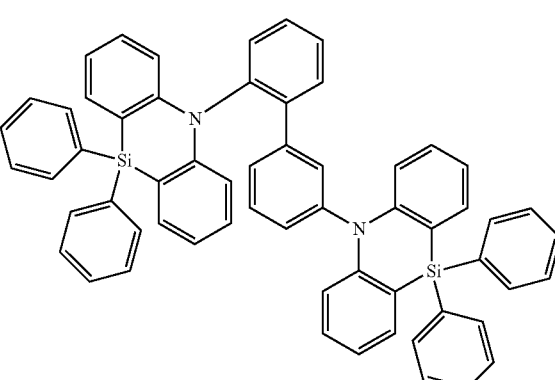

26

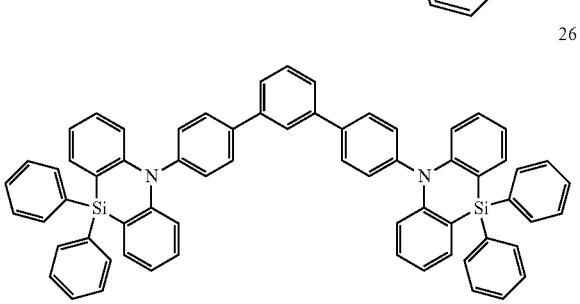

27

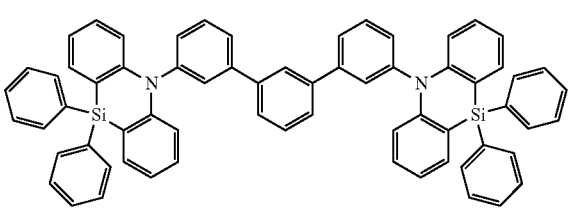

6. An organic electroluminescence device, comprising:
a first electrode;
a hole transport region disposed on the first electrode;
an emission layer disposed on the hole transport region;
an electron transport region disposed on the emission layer; and
a second electrode disposed on the electron transport region,
wherein the hole transport region includes:
a hole injection layer;
a hole transport layer on the hole injection layer; and
an electron blocking layer between the hole transport layer and the emission layer, and wherein the electron blocking layer includes a polycyclic compound represented by the following Formula 1:

[Formula 1]

wherein, in Formula 1,

L is a substituted or unsubstituted arylene group having 6 to 30 ring carbon atoms, $R_1$ to $R_8$ are each independently a hydrogen atom, a deuterium atom, a halogen atom, a cyano group, a substituted or unsubstituted silyl group, an alkyl group having 1 to 20 carbon atoms, a substituted or unsubstituted aryl group having 6 to 30 ring carbon atoms, or a substituted or unsubstituted heteroaryl group having 2 to 30 ring carbon atoms, $a_1$ to $a_4$ are each independently an integer of 0 to 4, and $a_5$ to as are each independently an integer of 0 to 5.

7. The organic electroluminescence device as claimed in claim 6, wherein the polycyclic compound represented by Formula 1 has a lowest triplet energy level value of 3.2 eV or more.

8. The organic electroluminescence device as claimed in claim 6, wherein L is a substituted or unsubstituted phenylene group, a substituted or unsubstituted divalent biphenyl group, or a substituted or unsubstituted divalent terphenyl group.

9. The organic electroluminescence device as claimed in claim 6, wherein L is a substituted or unsubstituted fluorenylene group.

10. The organic electroluminescence device as claimed in claim 6, wherein L is a group represented by one of the following Formulae 2-1 to 2-8:

[Formula 2-1]
[Formula 2-2]
[Formula 2-3]
[Formula 2-4]
[Formula 2-5]
[Formula 2-6]
[Formula 2-7]
[Formula 2-8]

wherein, in Formulae 2-1 to 2-8, $R_9$ to $R_{25}$ are each independently a hydrogen atom, a deuterium atom, a halogen atom, a cyano group, a substituted or unsubstituted silyl group, an alkyl group having 1 to 20 carbon atoms, a substituted or unsubstituted aryl group having 6 to 30 ring carbon atoms, or a substituted or unsubstituted heteroaryl group having 2 to 30 ring carbon atoms, $R_9$ to $R_{25}$ are separate or combine with an adjacent group to form a ring, and $a_9$ to $a_{25}$ are each independently an integer of 0 to 4.

11. The organic electroluminescence device as claimed in claim 6, wherein the polycyclic compound represented by Formula 1 is represented by the following Formula 3:

[Formula 3]

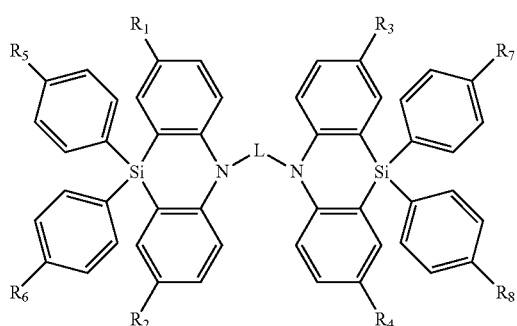

wherein, in Formula 3,

L is a substituted or unsubstituted arylene group having 6 to 30 ring carbon atoms, $R_1$ to $R_8$ are each independently a hydrogen atom, a deuterium atom, a halogen atom, a cyano group, a substituted or unsubstituted silyl group, an alkyl group having 1 to 20 carbon atoms, a substituted or unsubstituted aryl group having 6 to 30 ring carbon atoms, or a substituted or unsubstituted heteroaryl group having 2 to 30 ring carbon atoms, and at least one of $R_1$ to $R_8$ is a deuterium atom, a halogen atom, a cyano group, a substituted or unsubstituted silyl group, an alkyl group having 1 to 20 carbon atoms, a substituted or unsubstituted aryl group having 6 to 30 ring carbon atoms, or a substituted or unsubstituted heteroaryl group having 2 to 30 ring carbon atoms.

12. The organic electroluminescence device as claimed in claim 6, wherein:

$R_1$ to $R_8$ are each independently a hydrogen atom, a methyl group, a phenyl group, a fluorine atom, or a cyano group, and at least one of $R_1$ to $R_8$ is a methyl group, a phenyl group, a fluorine atom, or a cyano group.

13. The organic electroluminescence device as claimed in claim 6, wherein the polycyclic compound represented by Formula 1 is one the following Compounds 1 to 27:

1

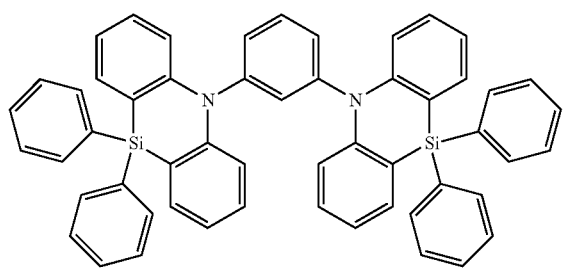

2

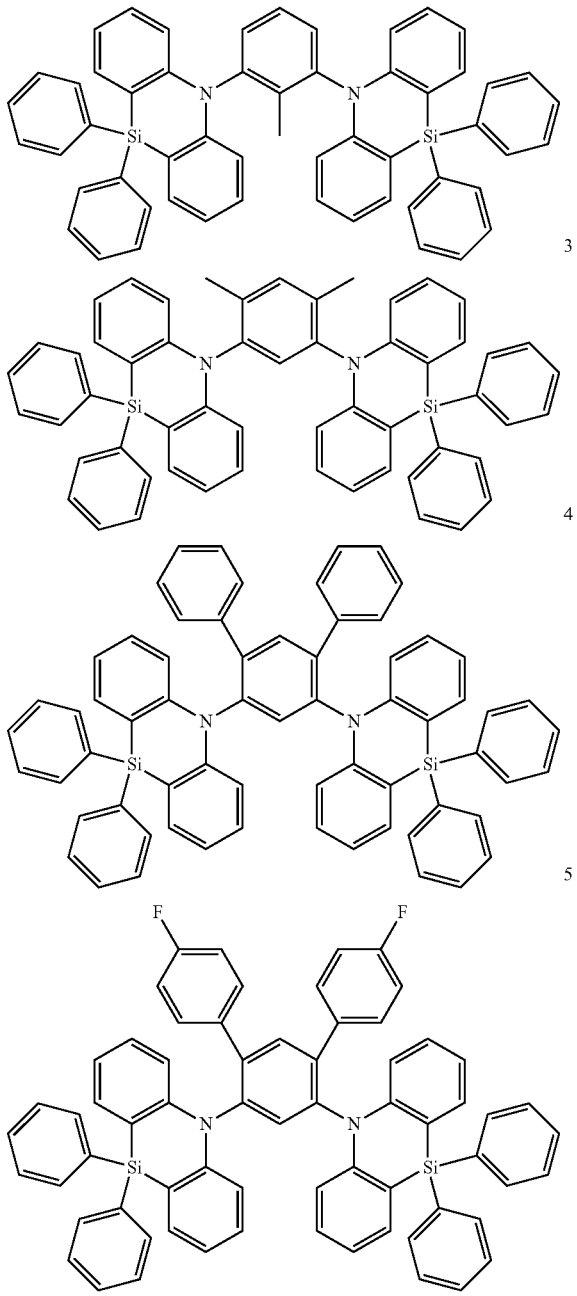

6

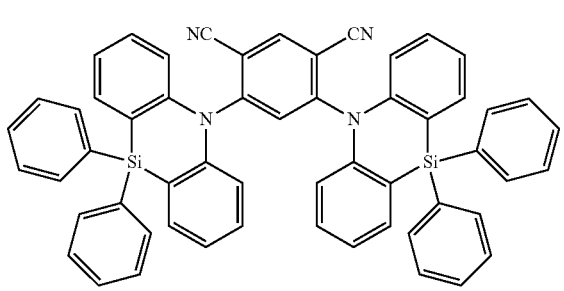

7
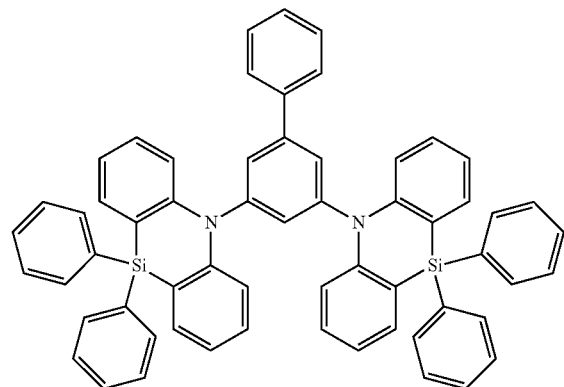
8
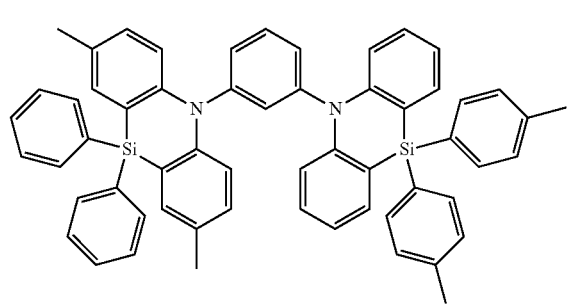
9
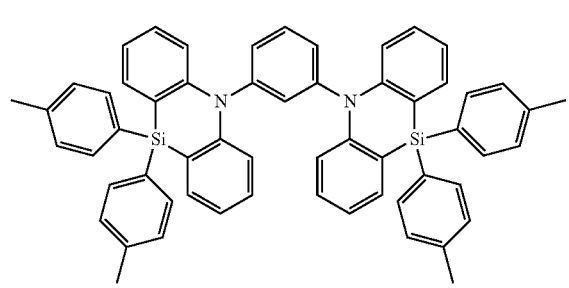
10
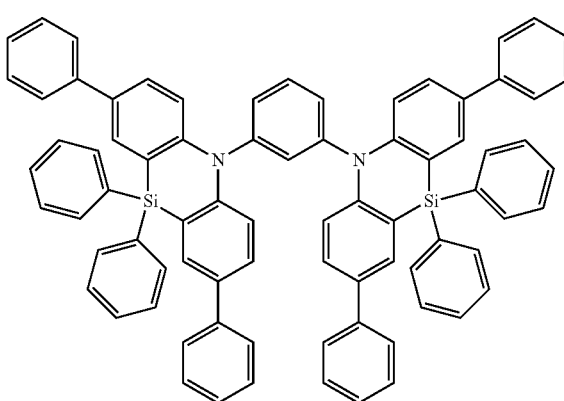
11
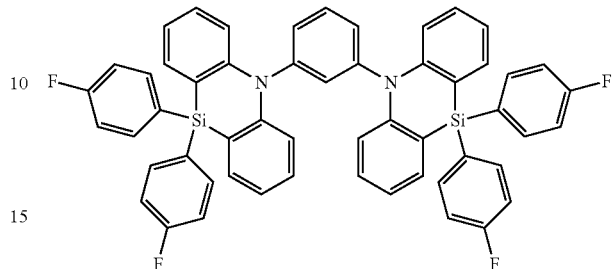
12
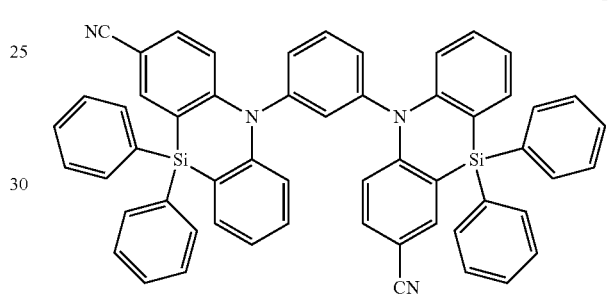
13
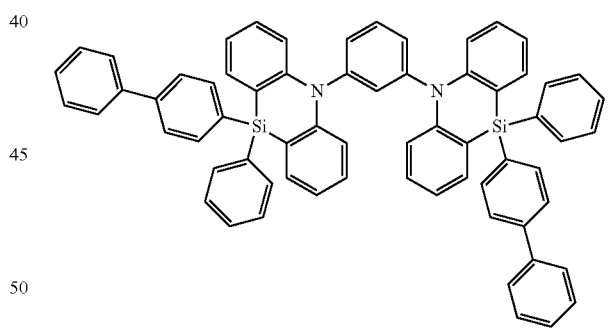
14
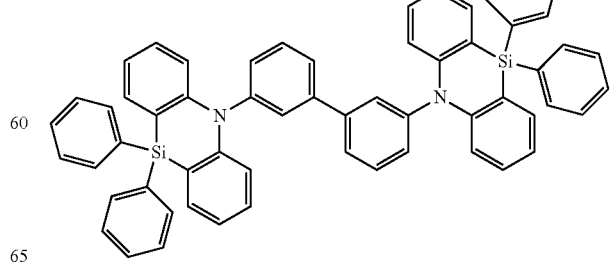

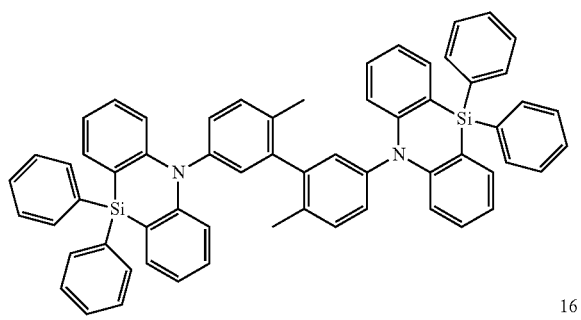
15
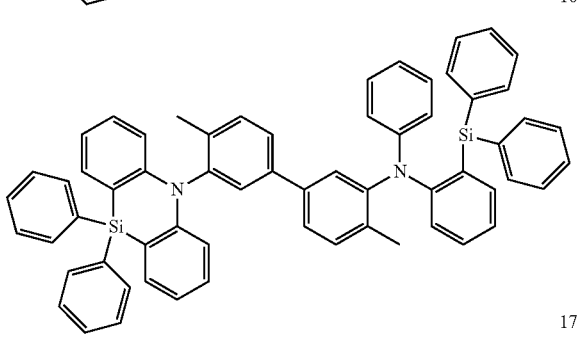
16
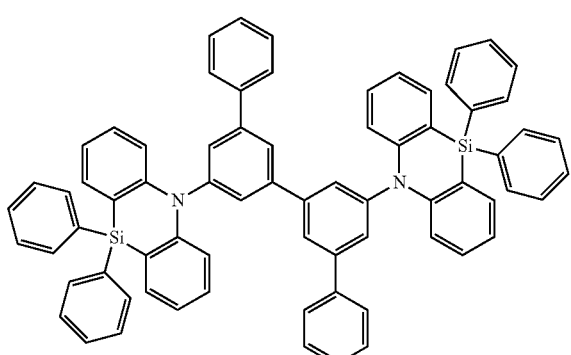
17
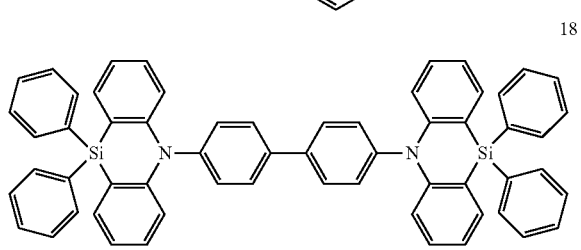
18
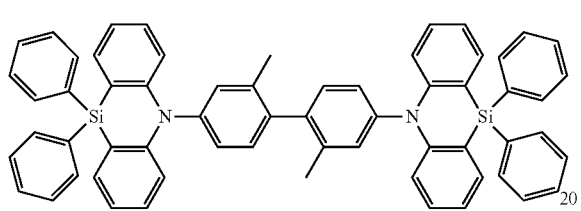
19
20
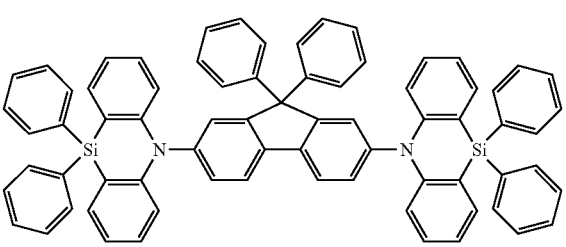
21
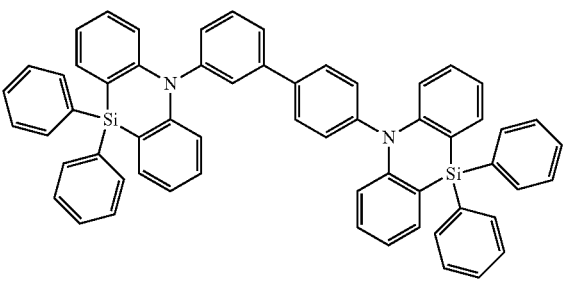
22
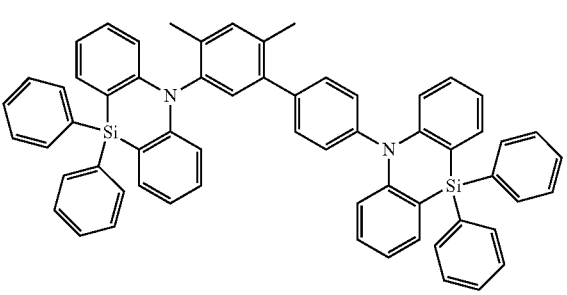
23
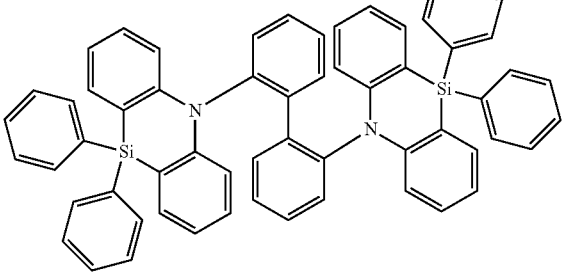
24
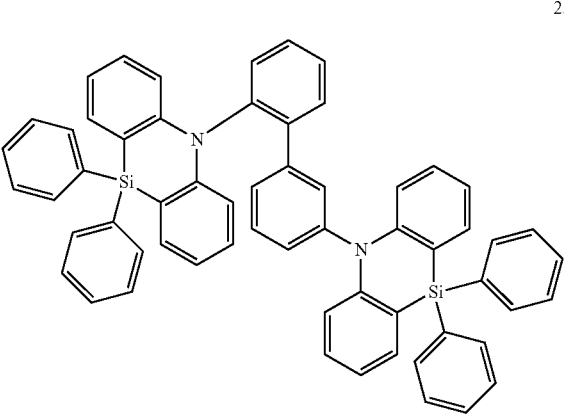
25

-continued
26
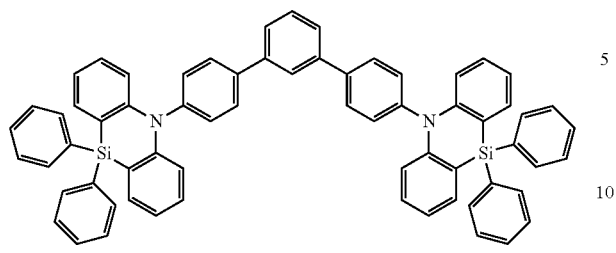
27
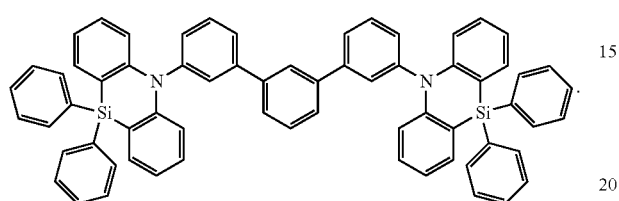
14. The organic electroluminescence device as claimed in claim 6, wherein the polycyclic compound represented by Formula 1 is a material emitting thermally activated delayed fluorescence (TADF) or a material emitting phosphorescence.
* * * * *

UNITED STATES PATENT AND TRADEMARK OFFICE
CERTIFICATE OF CORRECTION

PATENT NO. : 10,522,760 B2
APPLICATION NO. : 15/684112
DATED : December 31, 2019
INVENTOR(S) : Junta Fuchiwaki Page 1 of 1

It is certified that error appears in the above-identified patent and that said Letters Patent is hereby corrected as shown below:

In the Claims

Column 44, Line 54, Claim 1   delete "as" and insert --$a_8$--

Column 53, Line 32, Claim 6   delete "as" and insert --$a_8$--

Signed and Sealed this
Twenty-sixth Day of January, 2021

Drew Hirshfeld
*Performing the Functions and Duties of the*
*Under Secretary of Commerce for Intellectual Property and*
*Director of the United States Patent and Trademark Office*